(12) United States Patent
Tonyushkin

(10) Patent No.: US 10,261,141 B2
(45) Date of Patent: Apr. 16, 2019

(54) APPARATUS AND METHODS FOR SPATIAL ENCODING OF FFL-BASED MPI DEVICES

(71) Applicant: UNIVERSITY OF MASSACHUSETTS, Boston, MA (US)

(72) Inventor: Alexey Tonyushkin, Quincy, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 15/775,385

(22) PCT Filed: Nov. 11, 2016

(86) PCT No.: PCT/US2016/061524
§ 371 (c)(1),
(2) Date: May 10, 2018

(87) PCT Pub. No.: WO2017/083643
PCT Pub. Date: May 18, 2017

(65) Prior Publication Data
US 2018/0335487 A1    Nov. 22, 2018

Related U.S. Application Data

(60) Provisional application No. 62/254,551, filed on Nov. 12, 2015.

(51) Int. Cl.
*G01R 33/12* (2006.01)
*A61B 5/05* (2006.01)

(52) U.S. Cl.
CPC ........ *G01R 33/1276* (2013.01); *A61B 5/0515* (2013.01)

(58) Field of Classification Search
CPC .... A61B 5/0515; A61B 5/0035; G01R 33/307
See application file for complete search history.

(56) References Cited

U.S. PATENT DOCUMENTS

2001/0044152 A1* 11/2001 Burnett ................ G01N 21/253
436/43
2008/0309330 A1    12/2008 Ohyu et al.
(Continued)

FOREIGN PATENT DOCUMENTS

WO    2015028343 A1    3/2015

OTHER PUBLICATIONS

International Search Report and Written Opinion from corresponding International Application No. PCT/US2016/061524 dated Mar. 17, 2017.

*Primary Examiner* — Jermele M Hollington
*Assistant Examiner* — Alvaro Fortich
(74) *Attorney, Agent, or Firm* — Lando & Anastasi, LLP

(57) ABSTRACT

Selection-focus coils de-signed for 3D FFL-based MPI may allow for spatial encoding without additional shift coils and provide relatively large FOV and field gradient with very flat FFL. Additionally, a single-sided FFL-based device which is capable of 3D imaging is disclosed. With sufficient current amplitudes, FFL could encode the whole volume of a small animal or penetrate deep into human organs such as the vascular system or lymph nodes. An MPI device based on the proposed selection scheme could be a compact and robust alternative to the state-of-the-art FFP (FFL)-based MPI scanners.

31 Claims, 21 Drawing Sheets

(56) References Cited

U.S. PATENT DOCUMENTS

| | | |
|---|---|---|
| 2011/0089942 A1 | 4/2011 | Goodwill et al. |
| 2011/0221438 A1* | 9/2011 | Goodwill ............... G01R 33/10 |
| | | 324/301 |
| 2011/0234217 A1 | 9/2011 | Timinger |
| 2012/0126808 A1 | 5/2012 | Knopp et al. |
| 2012/0310076 A1 | 12/2012 | Buzug et al. |
| 2013/0241548 A1 | 9/2013 | Gleich et al. |
| 2014/0374159 A1* | 12/2014 | McElhinney ............. E21B 7/04 |
| | | 175/45 |
| 2015/0276902 A1 | 10/2015 | Weaver et al. |

\* cited by examiner

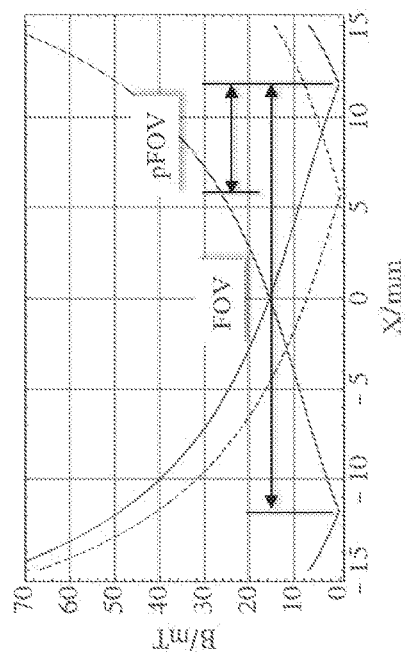
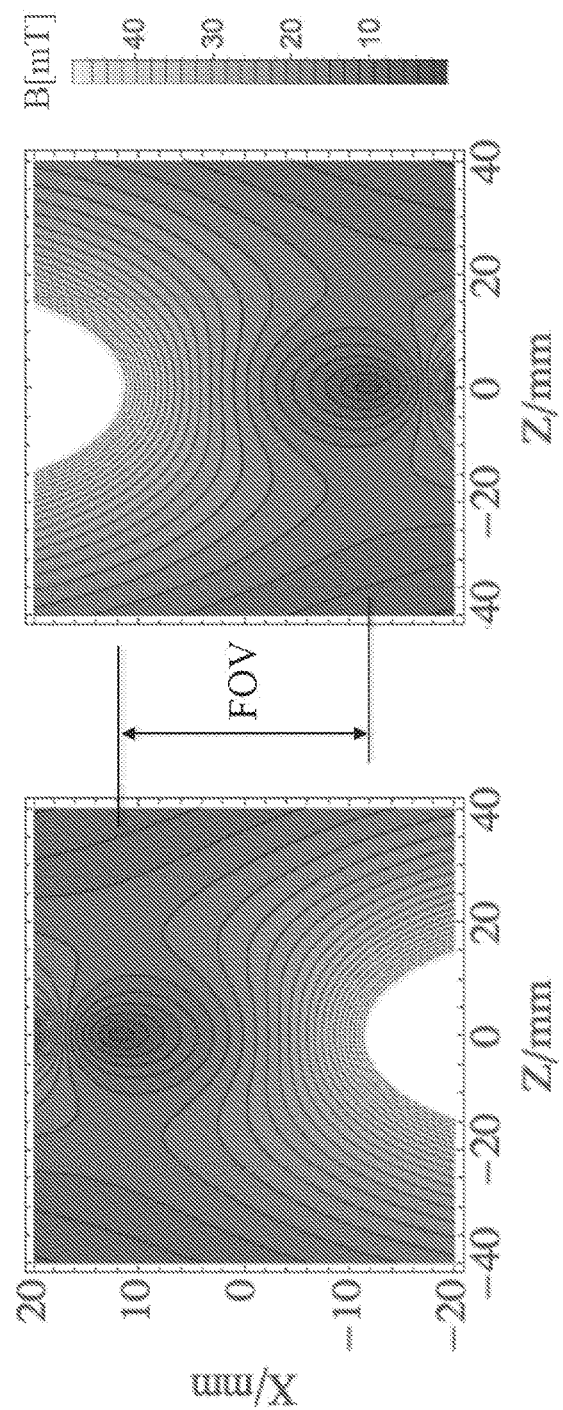
FIG. 11

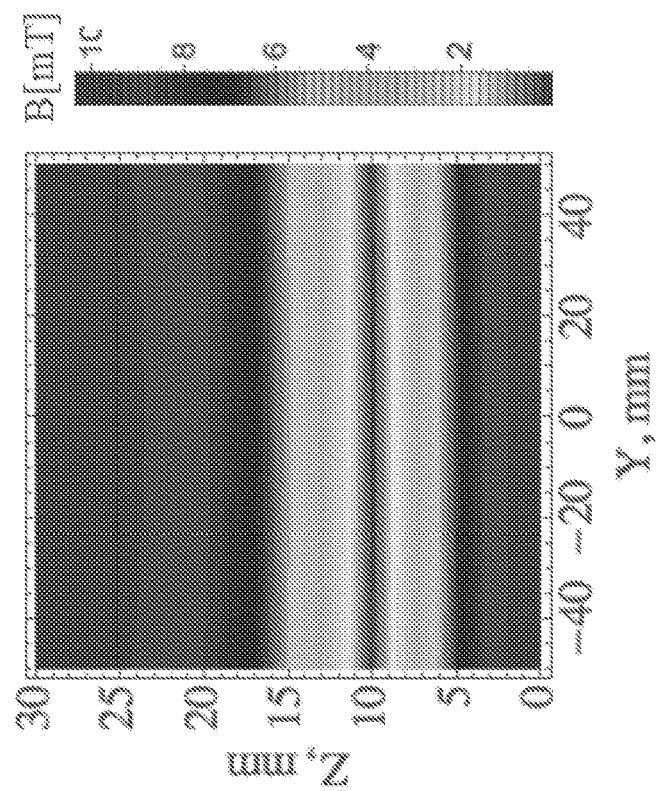
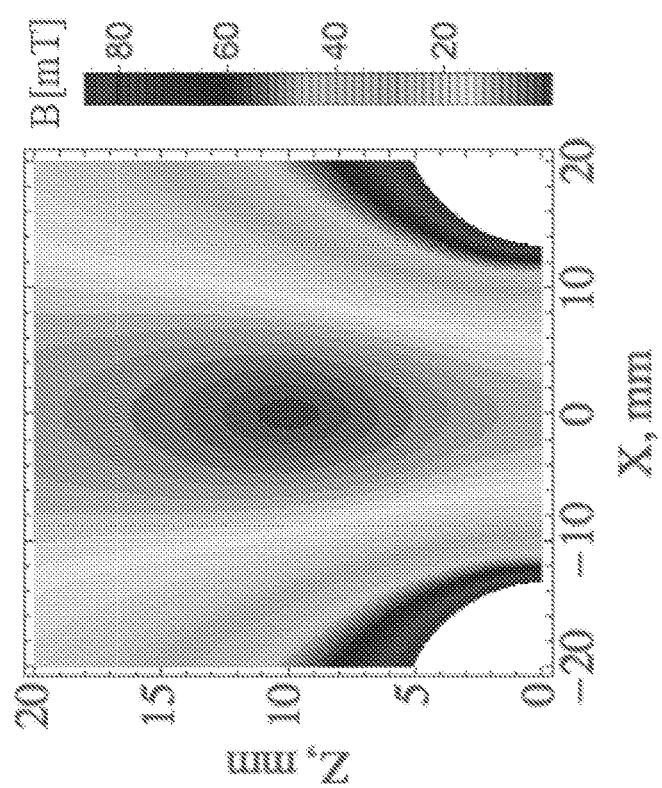
FIG. 3B

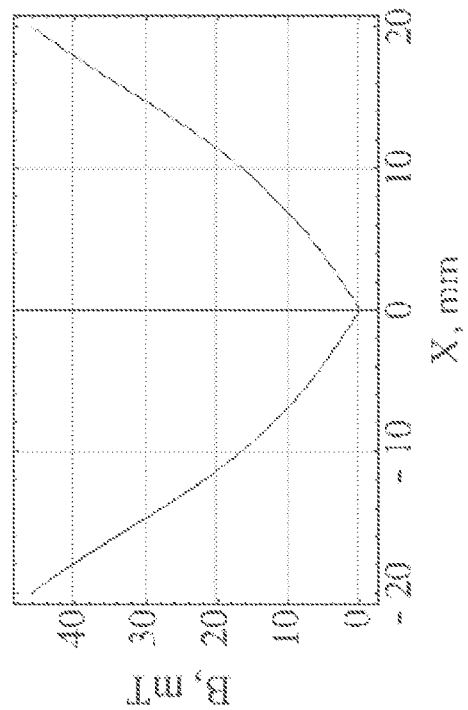
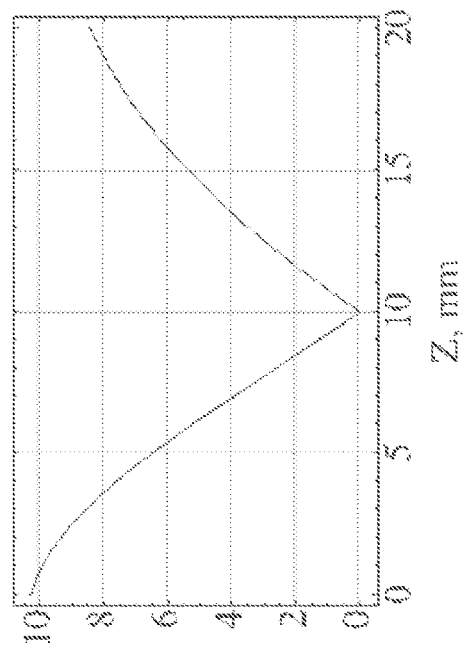
FIG. 3C

APPARATUS AND METHODS FOR SPATIAL ENCODING OF FFL-BASED MPI DEVICES

CROSS-REFERENCE TO RELATED APPLICATIONS

This application is a U.S. National Stage Application under 35 U.S.C. § 371 of International PCT Application No. PCT/US2016/061524 titled "APPARATUS AND METHODS FOR SPATIAL ENCODING OF FFL-BASED MPI DEVICES," filed Nov. 11, 2016, which claims priority under 35 U.S.C. § 119(e) to U.S. Provisional Application Ser. No. 62/254,551 titled "APPARATUS AND METHODS FOR SPATIAL ENCODING OF FFL-BASED DEVICES," filed Nov. 12, 2015, each of which is incorporated herein by reference in its entirety for all purposes.

BACKGROUND

Magnetic Particle Imaging (MPI) is an emerging, noninvasive medical imaging modality. MPI is a reconstructive imaging method, like Computed Tomography (CT) or Magnetic Resonance Imaging (MRI). There are two different types of magnetic field gradient geometries: field-free-point (FFP) and field-free-line (FFL).

SUMMARY

In accordance with one or more aspects, improved designs of FFL-based MPI scanners are disclosed. Specifically, various aspects relate to the design of magnetic gradient selection coils, arrangements of the scanner, and the associated spatial encoding methods.

The image quality using FFL is fundamentally better than those for FFP at the same super paramagnetic nanoparticles (SPIO) concentration. Previous experiments showed that the image with the highest SPIO concentration using FFP has a quality comparable to FFL images with only a tenth of the concentration. It has been shown theoretically that one would expect an improvement factor of 10 applying the rules of basic MRI theory. However, the creation of high magnetic gradients with FFL is much more challenging thus in practice the expected resolution of such devices is lower. Due to the lower resolution, the effective number of voxels in a line is lower than for FFP. Therefore the experimentally expected increase in sensitivity is lower than 10. In addition, from a technical point of view, it seems to be a considerable effort to achieve fast scanning with FFL.

In accordance with one or more aspects, significantly improved FFL-based devices that overcome the major challenges of FFL MPI scanners are disclosed. An FFL-based MPI device with in-plane projection and dynamic lateral encoding is disclosed. Selection coils and methods for a single-sided (also known as asymmetric) FFL 3D MPI scanner are disclosed. Compact selection coils based on permanent magnets for a single-sided FFL MPI scanner are also disclosed.

In accordance with one aspect, there is provided a field free line (FFL)-based magnetic particle imaging (MPI) device. The device comprises a first set of elongated electromagnets having lengths greater than widths and disposed along a common first axis, a second set of elongated electromagnets having lengths greater than widths and disposed along a common second axis, the common first axis being parallel to the common second axis and displaced from the common second axis in a direction normal to the common first axis, the second set of elongated electromagnets disposed directly over and overlapping the first set of elongated electromagnets in the direction normal to the common first axis, and a current generator. The current generator is configured to drive a first selection current in a first direction about the common first axis through an elongated electromagnet in the first set of elongated electromagnets and drive a second selection current in a second direction about the common second axis through an elongated electromagnet in the second set of elongated electromagnets. The second direction is opposite to the first direction. The elongated electromagnet in the second set of elongated electromagnets is disposed directly over the elongated electromagnet in the first set of elongated electromagnets in the direction normal to the common first axis. The first selection current and the second selection current create a selection magnetic field defining a field free line between the first set of elongated electromagnets and the second set of elongated electromagnets and parallel to a direction defined by the lengths of the elongated electromagnets.

In some embodiments, the current generator is further configured to drive a first focus current superimposed on the first selection current in an elongated electromagnet in the first set of elongated electromagnets, and drive a second focus current superimposed on the second selection current in an elongated electromagnet in the second set of elongated electromagnets disposed directly over the elongated electromagnet in the first set of elongated electromagnets in the direction normal to the common first axis. The first focus current and second focus current create a focus magnetic field displacing the field free line from a position centrally located between the first set of elongated electromagnets and second set of elongated electromagnets in a direction defined by widths of the elongated electromagnets.

In some embodiments, the current generator is further configured to drive an excitation field having a frequency of between about 20 kHz and about 100 kHz in at least one of the elongated electromagnets.

In some embodiments, the device further comprises a drive coil configured to generate an excitation field having a frequency of between about 20 kHz and about 100 kHz in a region defined between the first set of elongated electromagnets and the second set of elongated electromagnets.

In some embodiments, the first set of elongated electromagnets and the second set of elongated electromagnets are mounted on a rotating fixture configured to rotate the first set of elongated electromagnets and the second set of elongated electromagnets about an axis parallel to the common first axis and centrally located between the first set of elongated electromagnets and the second set of elongated electromagnets.

In some embodiments, the device is configured to provide three dimensional imaging of an object disposed between the first set of elongated electromagnets and the second set of elongated electromagnets.

In some embodiments, each of the elongated electromagnets has a length:width ratio of at least 5:1.

In some embodiments, the device further comprises permanent magnets having magnetic fields that contribute to the selection field.

In accordance with another aspect, there is provided a method of performing field free line (FFL)-based magnetic particle imaging (MPI) of an object. The method comprises positioning the object between a first set of elongated electromagnets having lengths greater than widths and disposed along a common first axis and a second set of elongated electromagnets having lengths greater than widths and disposed along a common second axis. The common first axis is parallel to the common second axis and displaced from the common second axis in a direction normal to the common first axis. The second set of elongated electromagnets is disposed directly over and overlapping the first set of elongated electromagnets in the direction normal to the common first axis. The method further comprises driving a first selection current in a first direction about the common first axis through an elongated electromagnet in the first set of elongated electromagnets, and driving a second selection current in a second direction about the common second axis through an elongated electromagnet in the second set of elongated electromagnets, the second direction being opposite to the first direction, the elongated electromagnet in the second set of elongated electromagnets being disposed directly over the elongated electromagnet in the first set of elongated electromagnets in the direction normal to the common first axis, the first selection current and the second selection current creating a selection magnetic field defining a field free line between the first set of elongated electromagnets and the second set of elongated electromagnets and parallel to a direction defined by the lengths of the elongated electromagnets.

In some embodiments, the method further comprises driving a first focus current superimposed on the first selection current in an elongated electromagnet in the first set of elongated electromagnets, and driving a second focus current superimposed on the second selection current in an elongated electromagnet in the second set of elongated electromagnets disposed directly over the elongated electromagnet in the first set of elongated electromagnets in the direction normal to the common first axis. The first focus current and second focus current create a focus magnetic field displacing the field free line from a position centrally located between the first set of elongated electromagnets and second set of elongated electromagnets in a direction defined by widths of the elongated electromagnets.

In some embodiments, the method further comprises driving an excitation field having a frequency of between about 20 kHz and about 100 kHz in at least one of the elongated electromagnets.

In some embodiments, the method further comprises exciting magnetic nanoparticles within the object with the excitation field.

In some embodiments, the method further comprises generating an excitation field having a frequency of between about 20 kHz and about 100 kHz in a region defined between the first set of elongated electromagnets and the second set of elongated electromagnets with a drive coil distinct from the first set of elongated electromagnets and distinct from the second set of elongated electromagnets.

In some embodiments, the method further comprises rotating the first set of elongated electromagnets and the second set of elongated electromagnets about an axis parallel to the common first axis and centrally located between the first set of elongated electromagnets and the second set of elongated electromagnets.

In some embodiments, the method further comprises generating a three dimensional image of the object utilizing a magnetic field generated by the first set of elongated electromagnets and the second set of elongated electromagnets.

In accordance with another aspect, there is provided a single-sided field free line (FFL)-based magnetic particle imaging (MPI) device comprising two inner elongated electromagnets having lengths greater than widths and displaced from one another in a direction defined by the widths of the two inner elongated electromagnets, two outer elongated electromagnets disposed on opposite sides of the two inner elongated electromagnets and displaced from the two inner elongated electromagnets in the direction defined by the widths of the two inner elongated electromagnets, each of the two inner elongated electromagnets and the two outer elongated electromagnets being parallel to one another, and a current source. The current source is configured to generate a first selection current in a first of the two inner elongated electromagnets, the first selection current travelling in a first direction about an axis of the first of the two inner elongated electromagnets, generate a second selection current in a second of the two inner elongated electromagnets, the second selection current travelling in a second direction about an axis of the a second of the two inner elongated electromagnets, the second direction being opposite the first direction, generate a third selection current in a first of the two outer elongated electromagnets, the third selection current travelling in a third direction about an axis of the first of the two outer elongated electromagnets, and generate a fourth selection current in a second of the two outer elongated electromagnets, the fourth selection current travelling in the third direction about an axis of the second of the two outer elongated electromagnets. The first selection current, second selection current, third selection current, and fourth selection current generate a magnetic field having a field free line parallel to the lengths of the elongated electromagnets displaced from surfaces of the elongated electromagnets in a direction parallel to the axes of the elongated electromagnets.

In some embodiments, the two inner elongated electromagnets and the two outer elongated electromagnets are disposed in a common plane.

In some embodiments, the device is configured to provide three dimensional imaging of an object disposed on a same side of the device as the field free line.

In some embodiments, the device further comprises a first focus elongated electromagnet disposed adjacent the first of the two outer elongated electromagnets, and a second focus elongated electromagnet disposed adjacent the second of the two outer elongated electromagnets. The current generator is configured to generate focus currents in the first and second focus elongated electromagnets that create a magnetic field causing the field free line to be displaced in a direction defined by the widths of the two inner elongated electromagnets and the two outer elongated electromagnets.

In some embodiments, the two inner elongated electromagnets and two outer elongated electromagnets are disposed on a rotating fixture configured to rotate the two inner elongated electromagnets and two outer elongated electromagnets about an axis parallel to the axes of the two inner elongated electromagnets and two outer elongated electromagnets and centrally located between the two inner elongated electromagnets and two outer elongated electromagnets.

In some embodiments, each of the two inner elongated electromagnets and two outer elongated electromagnets have length:width aspect ratios of at least 5:1.

In some embodiments, the device further comprises permanent magnets having magnetic fields that contribute to the selection field.

In accordance with another aspect, there is provided a method of performing field free line (FFL)-based magnetic particle imaging (MPI) of an object. The method comprises disposing the object on a side of a FFL-based MPI imaging device including two inner elongated electromagnets having lengths greater than widths and displaced from one another in a direction defined by the widths of the two inner elongated electromagnets, and two outer elongated electromagnets disposed on opposite sides of the two inner elongated electromagnets and displaced from the two inner elongated electromagnets in the direction defined by the widths of the two inner elongated electromagnets. Each of the two inner elongated electromagnets and the two outer elongated electromagnets are parallel to one another. The method further comprises generating a first selection current in a first of the two inner elongated electromagnets, the first selection current travelling in a first direction about an axis of the first of the two inner elongated electromagnets, generating a second selection current in a second of the two inner elongated electromagnets, the second selection current travelling in a second direction about an axis of the a second of the two inner elongated electromagnets, the second direction being opposite the first direction, generating a third selection current in a first of the two outer elongated electromagnets, the third selection current travelling in a third direction about an axis of the first of the two outer elongated electromagnets, and generating a fourth selection current in a second of the two outer elongated electromagnets, the fourth selection current travelling in the third direction about an axis of the second of the two outer elongated electromagnets. The first selection current, second selection current, third selection current, and fourth selection current generate a magnetic field having a field free line parallel to the lengths of the elongated electromagnets displaced from surfaces of the elongated electromagnets in a direction parallel to the axes of the elongated electromagnets.

In some embodiments, the method further comprises generating focus currents in first and second focus elongated electromagnets disposed adjacent the first and second outer elongated electromagnets, respectively, that create a magnetic field causing the field free line to be displaced in a direction defined by the widths of the two inner elongated electromagnets and the two outer elongated electromagnets.

In some embodiments, the method further comprises rotating the two inner elongated electromagnets and two outer elongated electromagnets about an axis parallel to the axes of the two inner elongated electromagnets and two outer elongated electromagnets and centrally located between the two inner elongated electromagnets and two outer elongated electromagnets.

In some embodiments, the method further comprises generating a three dimensional image of the object.

In accordance with another embodiment, there is provided a single-sided field free line (FFL)-based magnetic particle imaging (MPI) device comprising two vertically poled inner permanent magnets shaped as rectangular prisms having lengths greater than widths and heights. The two inner permanent magnets have equal magnetizations, also known as remanences. The device further comprises two vertically poled outer permanent magnets shaped as rectangular prisms having lengths greater than widths and heights. A first of the outer permanent magnets is disposed on a first side of the two inner permanent magnets in a direction defined by the widths of the two inner permanent magnets. A second of the outer permanent magnets is disposed on an opposite side of the two inner permanent magnets from the first of the outer permanent magnets, the two outer permanent magnets having equal magnetizations. The magnetizations of the two outer permanent magnets are greater than the magnetizations of the two inner permanent magnets. A magnetization vector of each adjacent permanent magnet is antiparallel to each other. The device further comprises two elongated electromagnetic coils disposed outside of the outer pair of the permanent magnets. A first of the elongated electromagnetic coils is disposed on a first side of the two outer permanent magnets in a direction defined by the widths of the two outer permanent magnets. A second of the elongated electromagnetic coils is disposed on an opposite side of the two outer permanent magnets from the first of the elongated electromagnetic coils.

In some embodiments, the outer permanent magnets and inner permanent magnets are parallel and overlap one another in a direction defined by the widths of the permanent magnets.

In some embodiments, the device comprises two sets of elongated electromagnetic coils disposed outside of the outer pair of the permanent magnets, a first set of the elongated electromagnetic coils disposed on a first side of the two outer permanent magnets in a direction defined by the widths of the two outer permanent magnets, a second set of the elongated electromagnetic coils disposed on an opposite side of the two outer permanent magnets from the first set of the elongated electromagnetic coils.

In some embodiments, the two sets of elongated electromagnetic coils include conductors wound about axes that are parallel to height directions of the permanent magnets.

In some embodiments, the first pair of the elongated electromagnetic coils are configured to create magnetic fields that displace a FFL created by a magnetic field generated by the permanent magnets to be displaced in a direction defined by the heights of the permanent magnets, and the device further comprises a current generator configured to supply alternating current to the first pair of the elongated electromagnetic coils.

In some embodiments, the first pair of elongated electromagnetic coils are disposed on opposite sides of the permanent magnets.

In some embodiments, the first pair of elongated electromagnetic coils are coplanar.

In some embodiments, the second pair of the elongated electromagnetic coils are configured to create magnetic fields that displace a FFL created by a magnetic field generated by the permanent magnets to be displaced in a direction defined by the widths of the permanent magnets, and the device further comprises a current generator configured to supply alternating current to the second pair of the elongated electromagnetic coils.

In some embodiments, the second pair of elongated electromagnetic coils are disposed on opposite sides of the permanent magnets.

In some embodiments, the second pair of elongated electromagnetic coils are coplanar.

In some embodiments, the device is disposed on a rotating fixture configured to rotate the device about an axis parallel to a heightwise direction of the permanent magnets and centered in the lengthwise and widthwise directions of the permanent magnets between the permanent magnets and electromagnetic coils.

In some embodiments, the two sets of elongated electromagnetic coils have lengths parallel to the lengths of the permanent magnets.

In some embodiments, the two sets of elongated electromagnetic coils include conductors wound about axes that are parallel to height directions of the permanent magnets.

In accordance with another aspect, there is provided a method of performing field free line (FFL)-based magnetic particle imaging (MPI) of an object. The method comprises disposing the object on a side of a FFL-based MPI imaging device including two vertically poled inner permanent magnets shaped as rectangular prisms having lengths greater than widths and heights, the two inner permanent magnets having equal magnetizations, two vertically poled outer permanent magnets shaped as rectangular prisms having lengths greater than widths and heights, a first of the outer permanent magnets disposed on a first side of the two inner permanent magnets in a direction defined by the widths of the two inner permanent magnets, a second of the outer permanent magnets disposed on an opposite side of the two inner permanent magnets from the first of the outer permanent magnets, the two outer permanent magnets having equal magnetizations, the magnetizations of the two outer permanent magnets being greater than the magnetizations of the two inner permanent magnets, a magnetization vector of each adjacent permanent magnet being antiparallel to each other, and two elongated electromagnetic coils disposed outside of the outer pair of the permanent magnets, a first of the elongated electromagnetic coils disposed on a first side of the two outer permanent magnets in a direction defined by the widths of the two outer permanent magnets, a second of the elongated electromagnetic coils disposed on an opposite side of the two outer permanent magnets from the first of the elongated electromagnetic coils. The method further comprises generating an alternating current in the two elongated electromagnetic coils.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing.

In the drawings:

FIG. 1I illustrates results of a simulation of transverse field focusing and encoding of the partial field of view in the Y-Z plane of an exemplary FFL MPI scanner design;

FIG. 3B illustrates results of a simulation of permanent magnet field quality in the X-Z and Y-Z planes of an exemplary single-sided FFL MPI scanner;

FIG. 3C illustrates results of a simulation of permanent magnet field quality along the Z-axis and X-axis of an exemplary single-sided FFL MPI scanner;

DETAILED DESCRIPTION

Figure 1A:
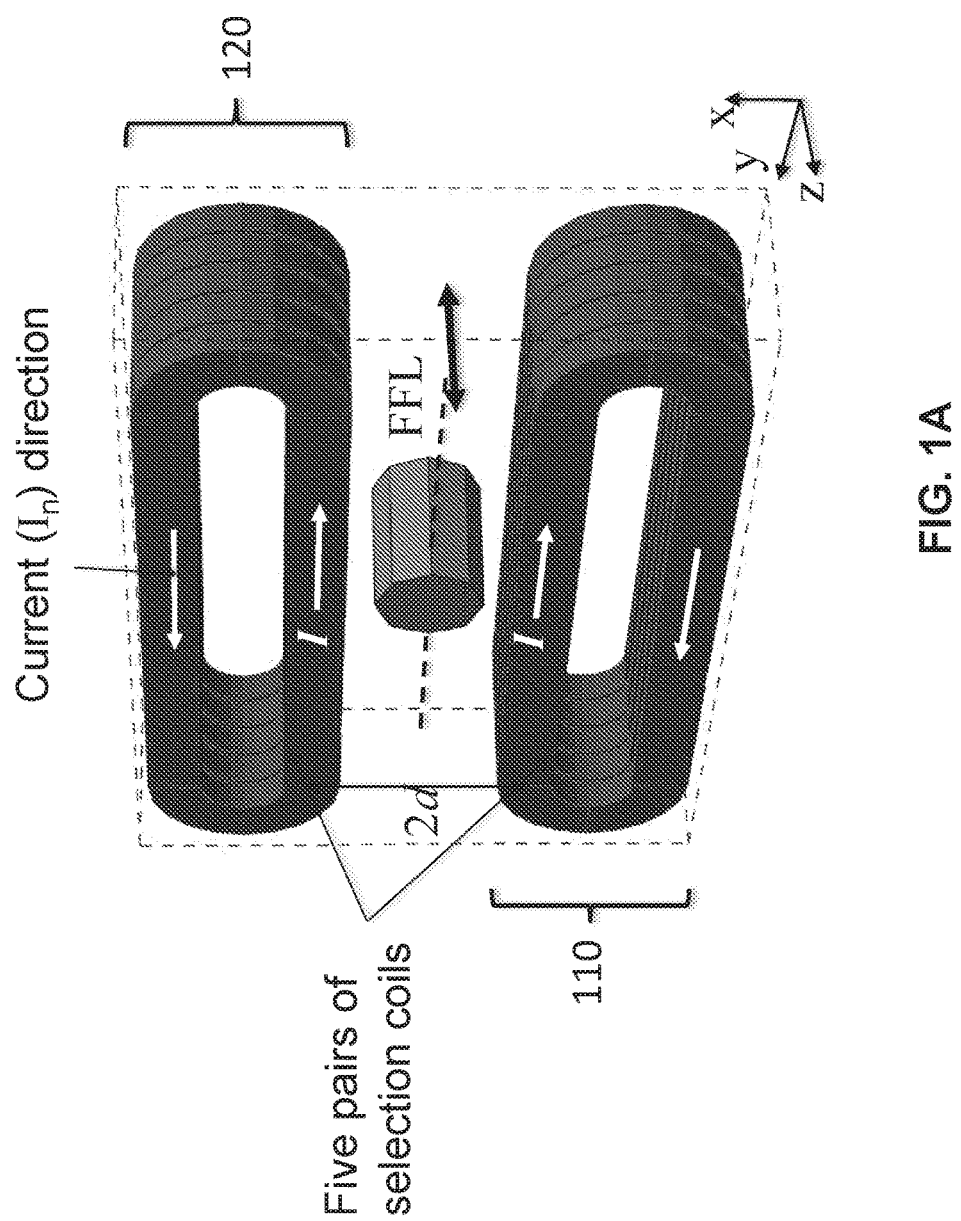
FIG. 1A is an isometric view of an embodiment of five pairs of selection coils for an exemplary FFL MPI scanner.

In accordance with one or more embodiments, systems and methods may provide robust three-dimensional (3D) spatial encoding for FFL as opposed to two-dimensional (2D) limited imaging. Significantly improved FFL-based devices that overcome the major challenges of FFL MPI scanners are disclosed. Increased field flatness may provide higher spatial resolution and increased field of view (FOV). A simplified design may reduce the complexity of MPI devices and may be more power efficient. For example, the systems may not require separate focus and drive coils. FFL selection coils for MPI are disclosed. A high magnetic gradient field may yield high spatial resolution MPI. A large FOV may beneficially be enabled along with a more open geometry design. The implementation of various encoding trajectories that combine mechanical rotation (0 to 180 degrees) and simultaneous longitudinal dynamical shift by the same selection coils that provide FFL may be enabled. In some embodiments, an FFL-based single-sided design with 3D imaging capability is disclosed. Such systems are robust, power efficient, and may beneficially be used for human or animal subjects or other objects.

An MPI image of an object's volume of interest may generally be generated in two steps. The first step, referred to as data acquisition, is performed using an MPI scanner. The MPI scanner has means to generate a static magnetic gradient field, often called the "selection field," which has a (single) field-free point (FFP) or a field-free line (FFL) at the isocenter of the scanner. It is surrounded by a low magnetic field strength, which is in turn surrounded by a higher magnetic field strength. By superimposing additional magnetic fields in time to the static selection field, the FFP or FFL may be moved along a predetermined FFP (FFL) trajectory throughout a "volume of scanning" surrounding the isocenter. This time-dependent magnetic field could be generated by AC current or physical motion in the selection coils themselves or using additional "drive coils." Drive coils, which may be separate coils or which may be the same coils that generate the static selection field, are needed in MPI to generate the rapidly changing magnetic field (25-1040 kHz), referred to herein as the "excitation field," that excites the magnetic particles of interest. Magnetic particles within vicinity of the FFP or FFL are excited by the excitation field and display a change in magnetization that may be detected, but magnetic particles within the region of high magnetic field strength outside the FFP or FFL are magnetically saturated and are not excited by the excitation field. The scanner also has an arrangement of one or more receive coils that detect the response of the particles from the excitation field by means of the voltages induced in these coils.

An object must contain magnetic nanoparticles (SPIO) or other magnetic non-linear materials to be imaged by MPI; if the object is an animal or a patient, a contrast agent containing such particles is administered to the animal or patient prior to the scan. During the data acquisition, the MPI scanner moves the FFP (FFL) along a deliberately chosen trajectory that covers the volume of scanning within the FOV of the scanner. The magnetic nanoparticles within the object experience a changing magnetic field and respond by changing their magnetization. The changing magnetization of the nanoparticles induces a time-dependent voltage in each of the receive coils. This voltage is sampled in a receiver associated with the receive coil. The samples output by the receivers are recorded and constitute the acquired data.

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the FOV. The reconstruction is generally performed by a dedicated computer, which executes a suitable computer program. The reconstruction algorithm is based on a mathematical model of the data acquisition.

MPI apparatus and methods have the advantage that they can be used to examine arbitrary examination objects, for example, human bodies in a non-destructive manner and with high spatial and temporal resolutions, both close to the surface and remote from the surface of the examination object. Since both static and low (kHz) frequency range magnetic fields are highly penetrable as long as there are no large metal objects present in the FOV, MPI has no fundamental limit in the scanning depth.

In accordance with one or more embodiments, the selection coils may include drive oscillating current that allow for encoding and signal production at the same time. No additional coils may be required apart from receive coils. The FFL may move rapidly back and forth along the Z-axis. (See FIG. 1A for definition of X, Y, and Z axes relative to the orientation of exemplary selection coils.) As discussed below, this may also be applicable to a single-sided design. The inner coils of a single-sided FFL MPI scanner may be driven with DC current and the outer coils may provide an oscillating field so that the height or displacement of the FFL in the Z-axis or X-axis, respectively, are also rapidly varied. In addition, the two inner coils could be replaced by permanent magnets to reduce the power consumption.

Devices and methods in accordance with various disclosed embodiments may beneficially be used for biomedical imaging, research, drug development, and clinical diagnostics such as cancer diagnostics and staging, material science such as for the synthesis of nanoparticles, as well as in material surveys applications.

1. Selection-Focus Field Coils for FFL-Based MPI Device with Dynamic Transverse and Longitudinal Encoding In accordance with one or more embodiments, an FFL-based device could potentially produce better image quality than an FFP-based device at the same nanoparticle concentration. However, from technical and safety limit points of view, generation of the required high strength magnetic gradient with FFL, which at the same time is capable of encoding a 3-D volume with the practical field-of-view (FOV), is challenging thus limiting either the expected resolution or reducing the FOV of such devices. In order to overcome this constraint a partial FOV (pFOV) MPI has been introduced for FFP, where a high magnetic field gradient is scanned over a small pFOV, while it is slowly focused to span the extended FOV. The present design of the combined selection-focus (SeFo) coils with FFL may offer a solution for FFL-based pFOV MPI scanners.

In general, to create FFL two parallel and oppositely directed elongated magnets are required. That way an FFL is created between the two magnets along the long dimension. These could be electromagnets or permanent magnets. A state of the art FFL MPI scanner uses two permanent magnets as static selection coils. The permanent magnets cannot move the FFL as is required to make 3D spatial encoding. Therefore, additional high power drive or bias coils are required that make the scanner less robust, less power efficient and thus more expensive. Without additional coils the full 3D encoding is problematic since there is no dynamic way to move the FFL. An alternative scheme uses multiple pairs of orthogonal circle Helmholtz coils for main selection and shift of FFL in 3D in a similar fashion to an FFP device. That design also proves to be bulky, low gradient strength, power inefficient, and provides limited FOV with low quality FFL.

In accordance with one or more embodiments, a SeFo coil geometry based on the electromagnets that are arranged in array of symmetrical pairs (see FIG. 1A) is provided. The SeFo coil arrangement illustrated in FIG. 1A includes five pairs of electromagnet coils, although in other embodiment, fewer or greater numbers of coil pairs may be utilized. A first set of the five pairs of coils 110 are arranged side by side along a common axis along the Z-axis. The five coils 110 are identical and fully overlap one another along the Z-axis. The electromagnets are elongated magnets having length dimensions along the Y-axis that are greater than their width along the Z-axis or height along the X-axis. In some examples, the electromagnet coils 110 have length to width ratios of greater than about 5:1, greater than about 10:1, or greater than about 15:1. In some examples, the electromagnet coils 110 have length to height ratios of greater than about 5:1, greater than about 10:1, or greater than about 15:1. In some examples, each of the five coils 110 of the electromagnets are formed of a low resistivity material, for example, copper and in some embodiments may be formed of superconducting materials. In one example, the coils of the electromagnets comprise copper tape having a width of about 6 mm and a height of about 13 mm. In other examples, the coils of the electromagnets comprise Litz wires that may include multiple filaments with various cross-sections. The electromagnets may include from about 20 to a few hundred windings of conductive material and may have an impedance of less than about 100 mΩ, for example, between about 10 mΩ and about 100 mΩ and an inductance between about 10 μH and 100 μH. In examples utilizing superconducting coils for the electromagnets, the electrical resistance of the coils would be zero. The electromagnets may, in use, be driven with currents between about 100 A and about 1,000 A or more. The electromagnets may include active cooling systems, for example, coolant lines passing through the coils or built into the coils themselves to circulate a coolant, for example, water, oil, or another coolant through the coils during operation. In some examples, the electromagnets are coreless, or include cores free of magnetic material. Further, the large number of high power electromagnets placed coaxially may require careful design of eddy current shielding that should be taken into the account for the actual construction design. Specifically, the required gap between the elements in the array may impact the longitudinal spatial resolution and FFL trajectory.

A second set of five coils 120 are arranged side by side along a common axis parallel to the Z-axis of FIG. 1A and displaced in the X-axis from the axis of the first set of five coils 110. The five coils 120 are identical and fully overlap one another along the Z-axis. The five coils 120 are oriented parallel to the five coils 110 and the five coils 120 are arranged directly over the five coils 110 in the X-axis. The five coils 120 may be substantially similar or identical in dimensions and construction as the five coils 110.

The coils 110, 120 are separated to define an imaging volume (cylinder) between the coils 110, 120. The FFL is generated at the center (half a coil's separation) of the volume along the length dimension of the coils (the Y-axis in FIG. 1A) when the coils 110, 120 are driven with currents of identical magnitudes. The FFL may be displaced from the center position if the currents through the coils 110, 120 are different. For example, if coils 110 are driven with a higher current than coils 120, the FFL will move closer to coils 120 than coils 110. Similarly, if coils 120 are driven with a higher current than coils 110, the FFL will move closer to coils 110 than coils 120. This allows the FFL to move along the X-axis illustrated in FIG. 1A to provide for scanning of a subject or object at various positions along the X-axis. Further, the coil pairs are arranged in array to enable longitudinal dynamic motion of the FFL along the Z-axis as explained in more detail below to provide for scanning of a subject or object at various positions along the Z-axis. The pair of coils 110, 120 are thus able to scan a subject or object in a two-dimensional plane defined by the Z-axis and X-axis. Each coil element (from either side of the imaging volume) is driven with time-dependent current so the direction of the current in each coil of the pair is symmetric with respect to FFL. A direct current component of current in each of the coils in coil array 110 is in the same direction. A direct current component of current in each of the coils in coil array 120 is in the same direction. A direct current component of current in coil segments of coils 110 and 120 proximate the imaging volume (the volume between the coils 110 and 120) is in the same direction. The direct current component of current in coils 110 and 120 create the selection field.

Figure 1B:
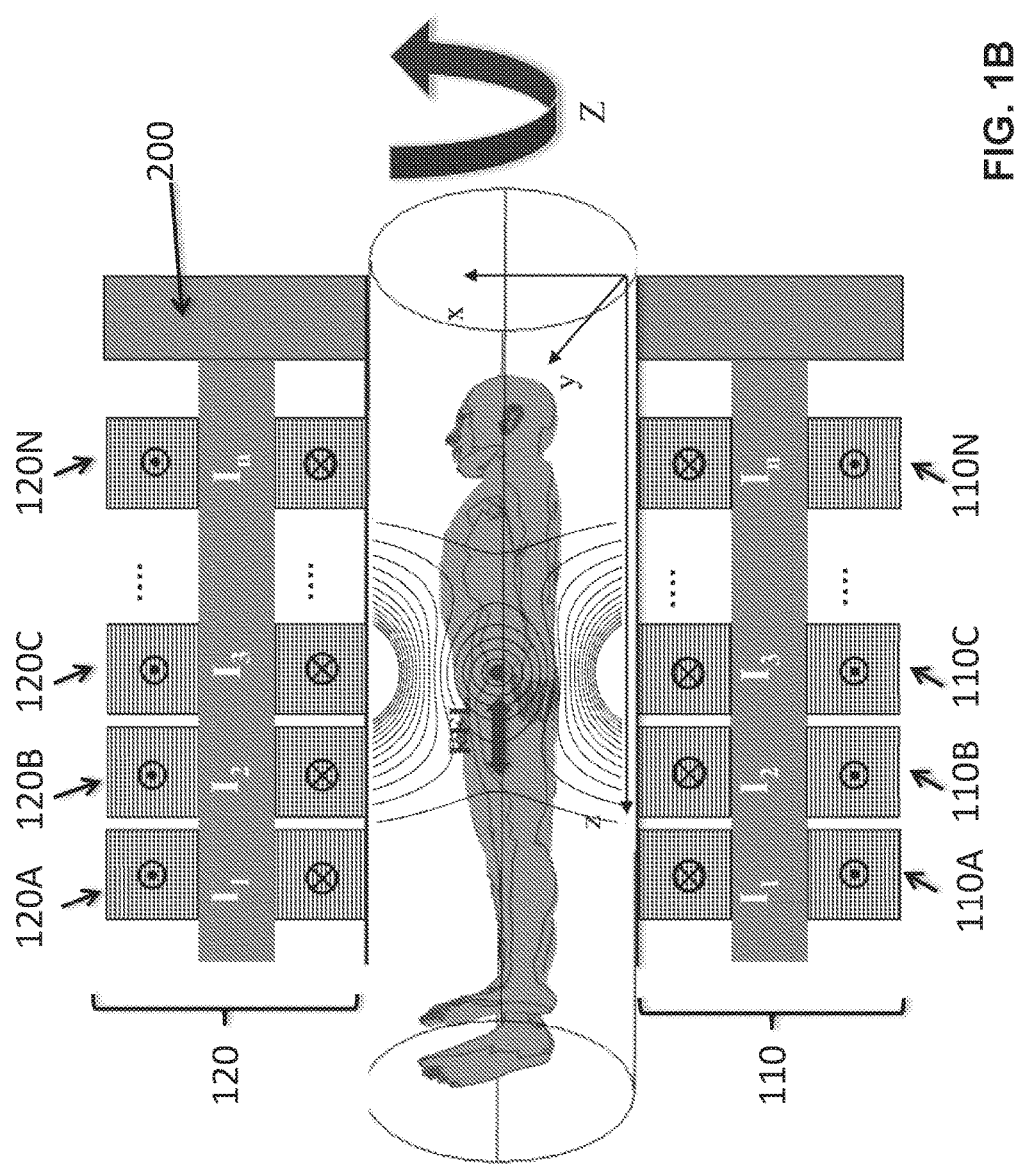
FIG. 1B is a cross-sectional view of an embodiment of an arrangement of electromagnets with instantaneous current pattern in an exemplary FFL, MPI scanner sized to image a human subject.
Figure 1C:
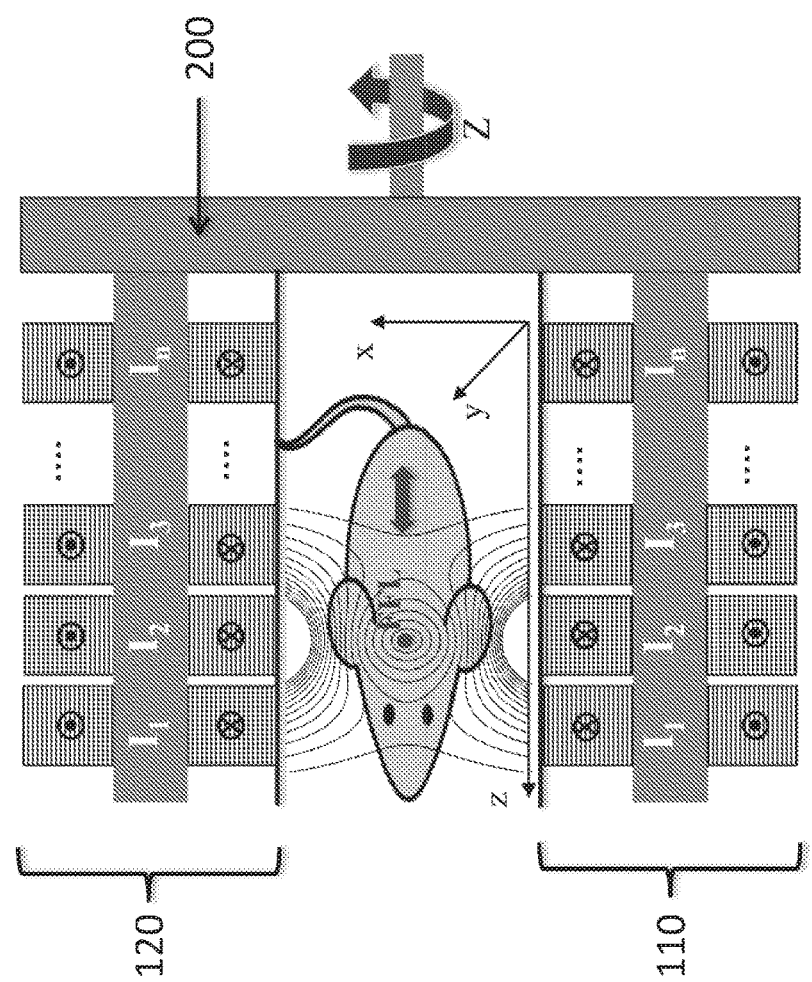
FIG. 1C is a cross-sectional view of an embodiment of an arrangement of electromagnets with instantaneous current pattern in an exemplary FFL MPI scanner sized to image a small animal subject.

An arrangement of electromagnet coils similar to that illustrated in FIG. 1A is illustrated in FIG. 1B with a human subject illustrated in the FOV of the selection coils. An arrangement of electromagnet coils similar to that illustrated in FIG. 1B is illustrated in FIG. 1C with a mouse illustrated in the FOV of the selection coils. The coils in FIGS. 1B and 1C are mounted on a rotatable fixture 200 that allows the coils to be rotated about the human or mouse subject or other object about the Z-axis to allow for 3D imaging of the human or mouse subject or other object. The number of coils n may be selected to accommodate a desired FOV along the Z-axis.

Each pair of coils in the array is fed independently with a programmed current generator according to the desired FFL longitudinal (Z-axis) time dependence. For example, if coil pair 110A, 120A has a peak current amplitude $I_1 = I_{max}$ and all the other pairs have zero current the FFL will be located at $Z=Z_1$ in the symmetry axis, X=0, between the first pair of coils 110A, 120A. If the current is switched so that $I_1 = 0$ and $I_2 = I_{max}$ then the FFL moves along the Z-axis to be located at $Z=Z_2$ in the symmetry axis of the second pair of coils 110B, 120B. The number of coil pairs in the arrays of coils 110, 120, the gap between them, and the thickness of the conductor define the longitudinal FOV that has no fundamental constraints.

The in-plane image encoding may be done by x-space imaging with projection image reconstruction in a similar fashion as used in modern CT scanners as well as other 2D (and 3D) FFL MPI devices. Specifically, in accordance with the present embodiments, the coil array (or the subject or object itself) is mechanically rotated around the FOV (Z-axis) up to 180 degrees. See, e.g., FIGS. 1B and 1C showing human scale and small animal scale devices, respectively. Rotating fixture 200 may be utilized to mechanically rotate the electromagnet arrays about the FOV and human or mouse with the axis of rotation of the rotating fixture 200 being along Z-axis centered between the arrays of coils 110, 120 in both the X-axis and Y-axis. The data are acquired at each rotated angle to create a projection along FFL and reconstructed by computer software using well-established mathematical algorithms such as Radon transformations. If the current is switched in the array at each rotation step it can encode various FFL trajectories in 3D space allowing application of various imaging algorithms. For example, a single 180 degree rotation around the Z-axis with simultaneous (linear) advancing of the current along the array would encompass a spiral trajectory in 3D volume.

Figure 1D:
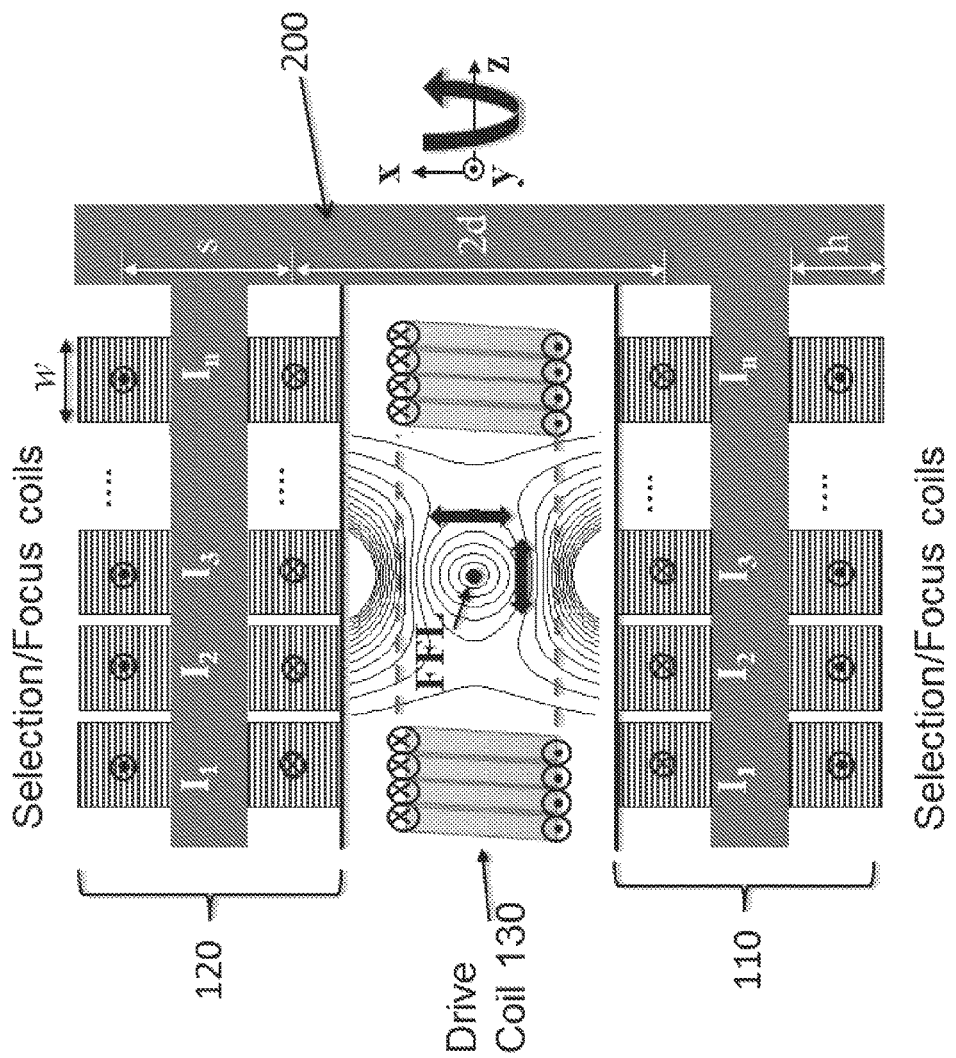
FIG. 1D illustrates an embodiment of an arrangement of electromagnets in an exemplary FFL MPI scanner including separate selection/focus and drive coils.

In the present design, the longitudinal driving magnetic field is combined with SeFo field that reduces overall complexity of the device. An alternating current component may be superimposed on the direct current component of current through coils 110, 120, to create an excitation field superimposed on the selection-focus field. The excitation field is used to excite the magnetic nanoparticles in the FFL in the subject or object being imaged. The excitation field may have a frequency between about a few kHz to about 100 kHz and an amplitude of between about 100 A and about 1,000 A. In other examples, for transverse excitation additional Helmholtz pairs or solenoid drive coils could be implemented in the present design to superimpose oscillation onto the SeFo fields. Such coils could be (but not limited to) positioned concentrically with imaging FOV. See FIG. 1D illustrating a coils design including separate drive coils 130 for generating an excitation field in addition to the selection-focus coils 110, 120. In FIG. 1D 2$d$ is the coils' separation, w is the width of the conductor tape, s is the effective core width of the electromagnetic coil, h is the total thickness of the conductor, $I_n$ is the current in the n-th element with denoted instantaneous current pattern. The actual choice of the solenoid drive coil impacts the field quality in transverse pFOV operation regime. While the magnetic field from finite length solenoid coil cannot be made perfectly uniform, wider transverse dimensions may help to ensure the linearity of FFL. Since the disclosed SeFo coils design offers open geometry along the FFL a rectangular cross-section solenoid coil with an elongated side along Y-axis can be used.

The receive coils (not shown) are positioned inside the imaging chamber and close to the imaging volume. In some examples, it can be beneficial to use a multichannel receive array in a similar fashion to MRI receive coil technology. Such coils can be positioned along the cylindrical FOV with each element consisting of a solenoid and two pairs of saddle X,Y-axis coils.

In terms of a desired human sized MPI device (FIG. 1B) the main challenge is the creation of a strong magnetic field gradient, which contradicts with the required large spacing to accommodate a human. If such a device is built the present design would be very attractive as it only requires a pair of strong current coils (for in plane encoding); it has a relatively open geometry (Y-axis) design and therefore the spacing along X-axis could be minimized to allow for a higher magnetic gradient.

In accordance with one or more embodiments, the SeFo coils are based on the electromagnets that are arranged in symmetrical pairs. See FIG. 1A. The coils are separated by a distance d, which defines the in-plane FOV. The FFL is generated along the Y-axis at the symmetry axis, X=0, of the pair of coils with the magnetic gradient scaled as $\sim 1/d^2$. The coil pairs are arranged in a linear array to enable longitudinal (Z-axis) displacement of the FFL with an oscillating pattern. The in-plane image encoding may be done by x-space imaging method with projection image reconstruction. Specifically, the coil array is mechanically rotated around the Z-axis up to 180°. If the current is simultaneously oscillated in the array and the array (or a subject or object being imaged) is rotated, for example, 3D volume may be encoded.

In some embodiments, the entire MPI device may be shielded, for example, with a Faraday cage to prevent external electromagnetic noise from interfering with the excitation and receive fields thus impacting the quality of the images captured by the device.

One example of a method of operating the FFL MPI scanner of FIG. 1D is as follows: The current $I_n$ in each pair of coils in the array is independently controlled according to the desired FFL translation pattern as a function of time. For example, if only the first coil pair has a non-zero current $I_1=I_{max}$ the FFL will be located in the symmetry axis between the first pair of coils. By ramping down (up) the current $I_1$ ($I_2$) in the element one (two) the FFL can be smoothly advanced along Z-axis to the symmetry axis of the second pair of coils without FFL deformation or hops in transverse plane, and so on. By modulating the current in the adjacent elements (i.e. n−1 and n+1) of SeFo coils with $f_0 \approx 20$ kHz it is possible to oscillate FFL along the Z-axis to encode longitudinal pFOV while relatively slow shifting with $f_s \approx 100$ Hz between the elements allows translation of pFOV to encode extended FOV. The number of elements in the array, the gap between them, and the thickness of the conductor define the longitudinal extended FOV.

The transverse (XY-plane) encoding is done by focusing FFL with independently controlled current in the top $I_n^t$ and bottom $I_n^b$ coils so that $I_n^t \neq I_n^b$ thus providing shift of pFOV. The excitation within each transverse pFOV is created by fast oscillation of FFL by means of a drive solenoid coil driven with AC current:

$$I(t)=I_0 \sin(2\pi f_0 t),$$

where $I_0$ is the current amplitude, which is chosen to provide up to $B_{max} \approx 15$ mT$_{pp}$ of safe field, $f_0=25$ kHz is the oscillating frequency. A complete 3-D imaging is made possible by mechanical rotation of the required elements or the whole structure of the array around Z-axis up to 180° enabling x-space imaging with the projection image reconstruction. The receive coil assembly consists of a solenoid and saddle-shape coil pairs, which are located inside the solenoid drive coil along the Z-axis and X,Y-axis respectively.

To study the magnetic field generated by the symmetric array of electromagnetic coils simulations were performed using Wolfram Mathematic® software with Radia package (ESRF France). The package allows calculating the magnetic flux density B (also called magnetic B field) of electromagnetic coils by utilizing boundary Integral Methods.

For proof-of-principle, a five-element array was simulated, each element consisting of 30-cm-long electromagnetic coils. Each simulated coil has N=40 windings of a copper tape with w=6:33 mm, s=32 mm, h=13 mm, and coils separation of 2d=50 mm.

Figure 1E:
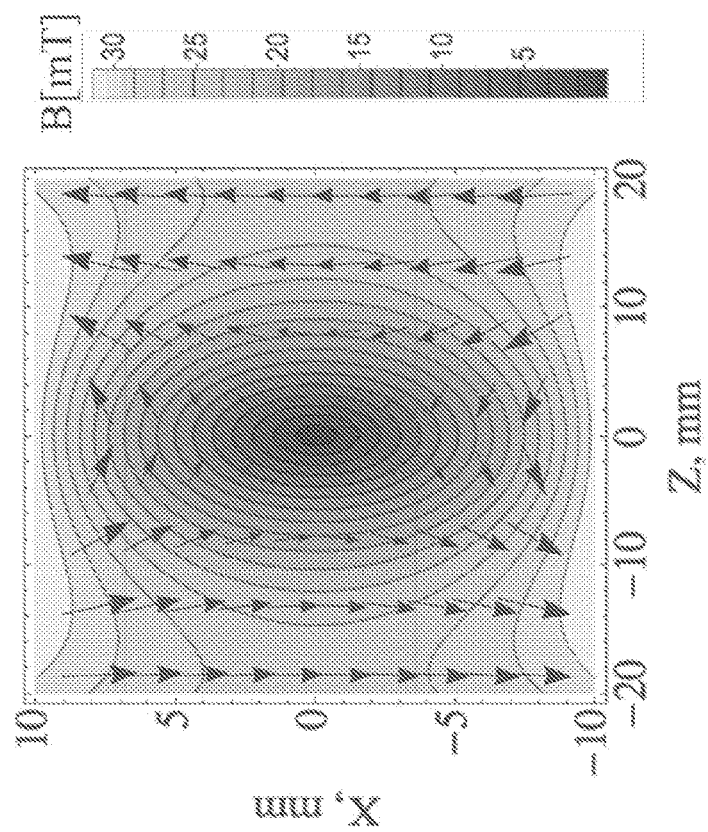
FIG. 1E illustrates results of a simulation of magnetic field quality in the X-Z plane of an exemplary FFL MPI scanner design.
Figure 1F:
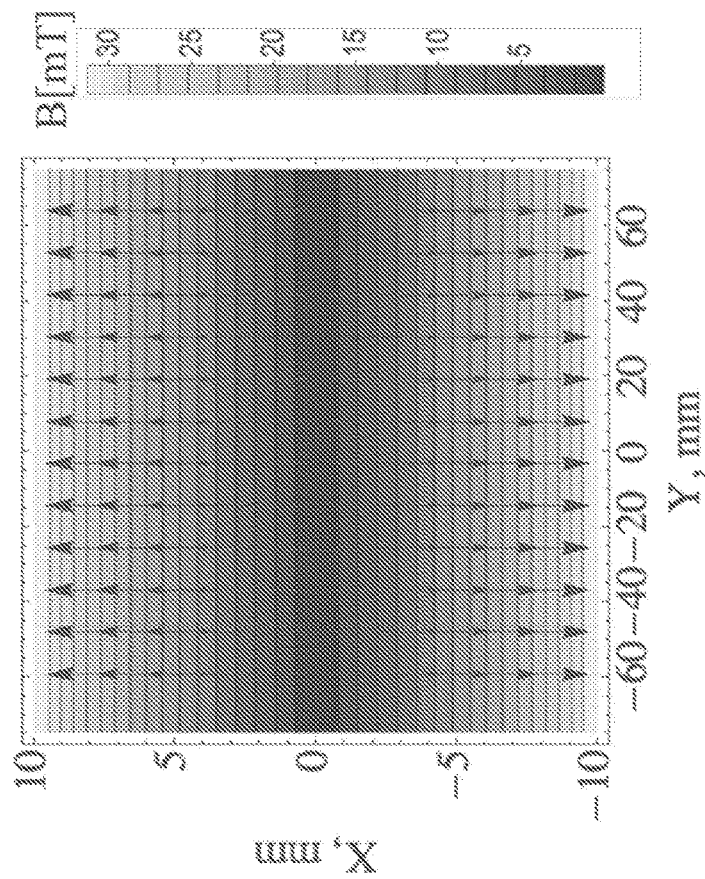
FIG. 1F illustrates results of a simulation of magnetic field quality in the X-Y plane of an exemplary FFL MPI scanner design.

FIGS. 1E and 1F show the simulated magnetic field pattern produced by a single element of SeFo coils with a reference current $I_{max}$=100 A in the X-Z and X-Y planes, respectively. It is seen from FIGS. 1E and 1F that the FFL is extremely flat across the region of more than a half of the length of the coil. In a practical device with the transverse FOV that is limited by the separation of the coils the length of the coils can be decreased up to the separation 2d without sacrificing the quality of FFL in the FOV.

Figure 1G:
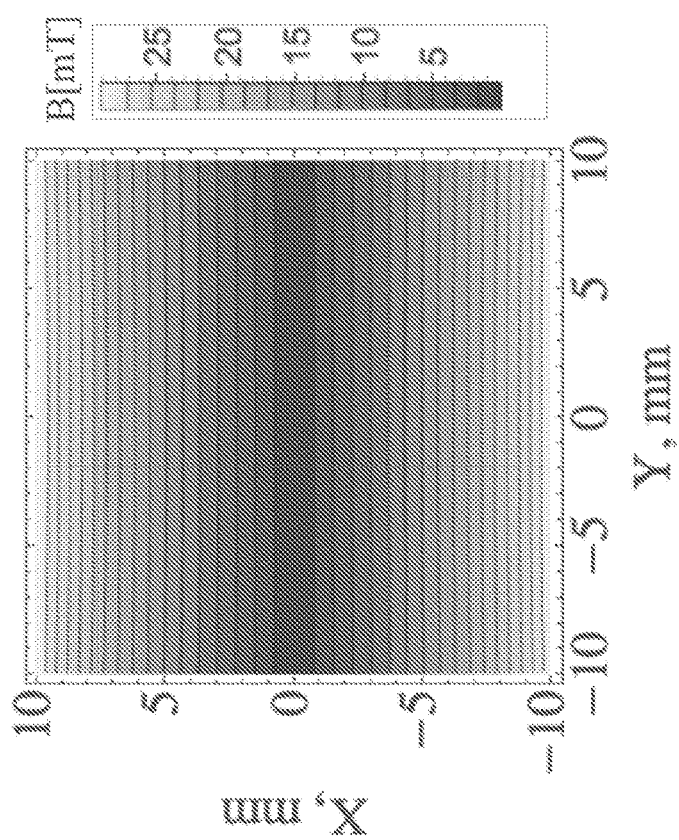
FIG. 1G illustrates results of a simulation of magnetic field contours in the X-Y plane of an exemplary FFL MPI scanner design.
Figure 1H:
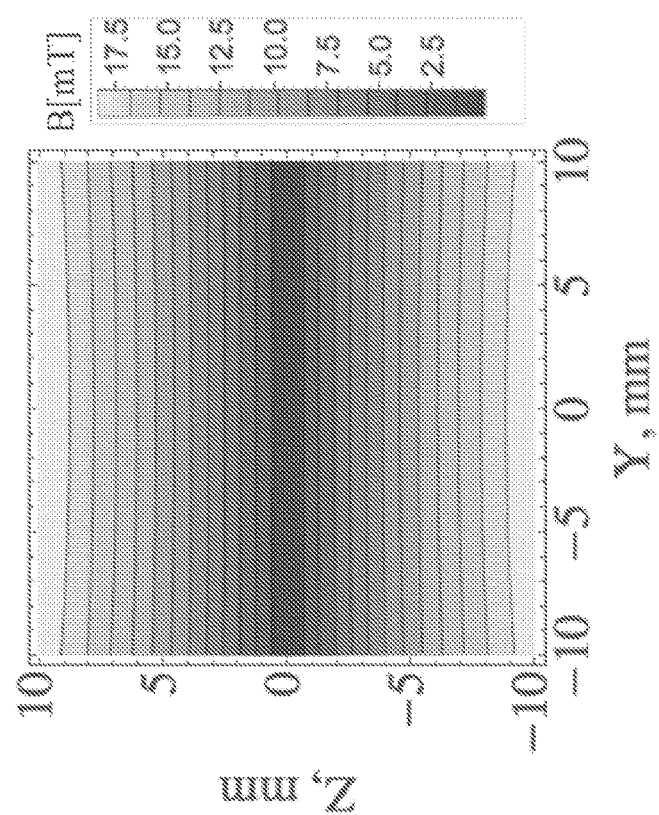
FIG. 1H illustrates results of a simulation of magnetic field contours in the Y-Z plane of an exemplary FFL MPI scanner design.

FIGS. 1G and 1H show the results of simulations of the magnetic field for 5-cm-long electromagnetic coils in the X-Y and Z-Y planes, respectively. Similarly, the shape of FFL does not degrade within FOV due to a symmetric current pattern in each element.

The example of SeFo coils performance in transverse focusing regime is shown in FIG. 1I. Full FOV encoding with $\Delta X$=24 mm is done by ramping up (down) the currents in the top $I^t$=20–100 A and bottom $I^b$=100–20 A coils respectively, and pFOV encoding of $\Delta X$=6 mm is done by an external uniform bias field, which can be produced by a solenoid coil with AC current. Thus the full FOV is split into five pFOV with partial overlaps.

Figure 1J:
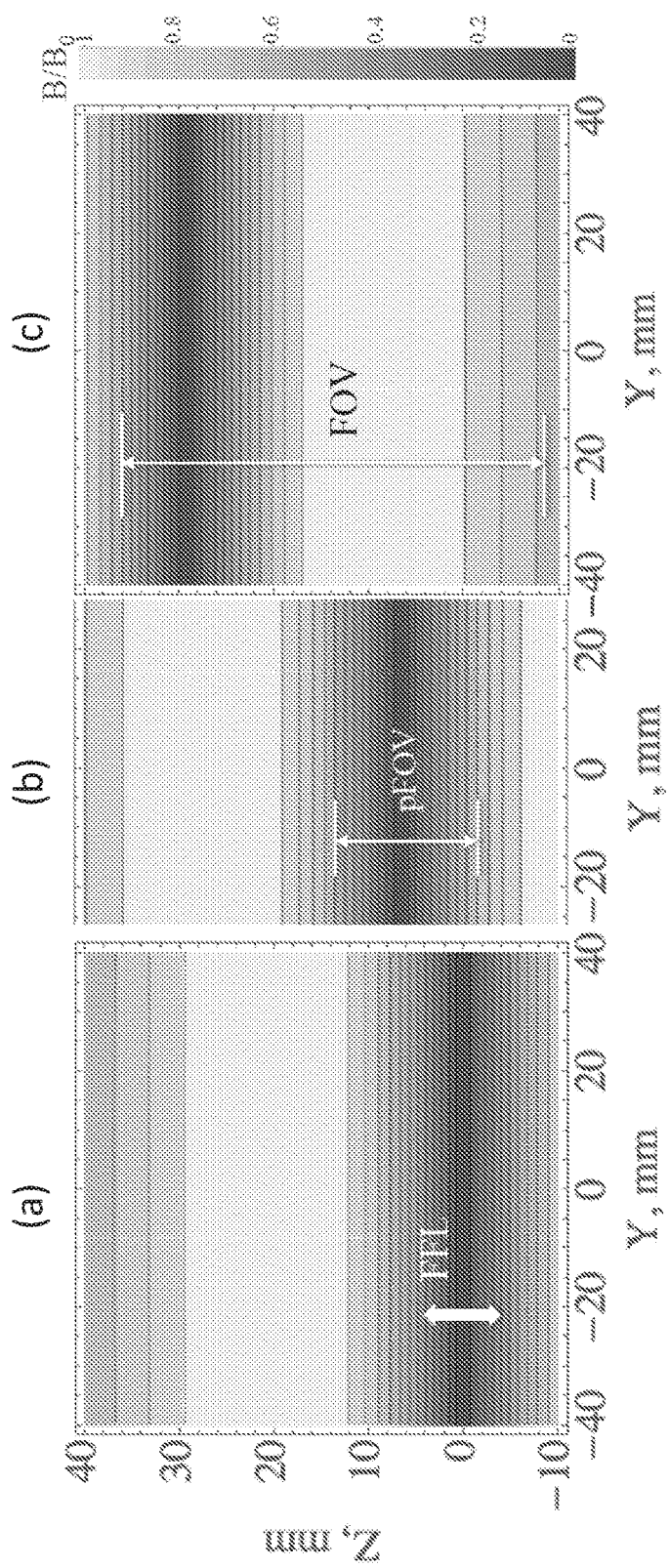
FIG. 1J illustrates results of a simulation of magnetic field contours in the Y-Z plane of an exemplary FFL MPI scanner design showing longitudinal field focusing and encoding of the partial field of view of the scanner.

For the operation with the extended longitudinal FOV, to advance the center of the pFOV along Z-axis the current in each element of the array is switched in a certain pattern, which is defined by the image reconstruction method. FIG. 1J shows the simulated magnetic field in pFOV created by the first, second, and last elements. The current in the array is ramped up (down) so that the instantaneous FFL position is given by the following pattern: a) $I_1$=100 A, b) $I_1$=10 A, $I_2$=90 A, and c) $I_5$=100 A. Such five-element array provides $\Delta Z$=3 cm separation between pFOV corresponding to the longitudinal extended FOV≈5 cm along Z-axis. An array with larger number of elements would allow increasing the longitudinal FOV.

The independent focusing in transverse and longitudinal directions with superimposed FFL rotation would allow a full image encoding. The temporal resolution is defined by the number of rotation steps and the rate of focusing in two directions.

2. Selection Coils Design and Method for a Single-Sided FFL 3D MPI Scanner

An MPI device has yet to be introduced to the clinical practice. The major challenge is to generate a sufficiently large gradient field that penetrates the whole body. An open geometry scanner will be also highly desirable. One way to make such a practical MPI device is to use a single-sided or asymmetric geometry. A single-sided device has all the hardware on one side from the imaging volume and therefore could be used on a whole body as well as a local volume imaging. The present hardware design for a single-sided device may be capable of 3D imaging. Moreover, different from recent field-free-point (FFP) based developments, the present geometry utilizes a potentially more sensitive field-free-line (FFL) configuration.

A "single-sided device" refers to a scanner that has all the apparatus on one side of the imaging volume. Such devices could be used equally on small animals and humans, as well as a sensitive MPI 2D spectrometer for medical and material science surveying. Such devices could be a compact, robust, and relatively cheap diagnostic tools that could be used in clinical practice. Due to obvious geometrical constrains (lack of counteractive coils in parallel configuration) there is a significant challenge in the implementation of such devices. The disclosed FFL-based single-sided device may be capable of 3D image encoding. With sufficient gradient, FFL could travel across the whole volume of a small animal or penetrate deep enough into the human organs such as vascular system or lymph nodes, for example, for breast cancer screening and staging.

Figures 2A, 2B:
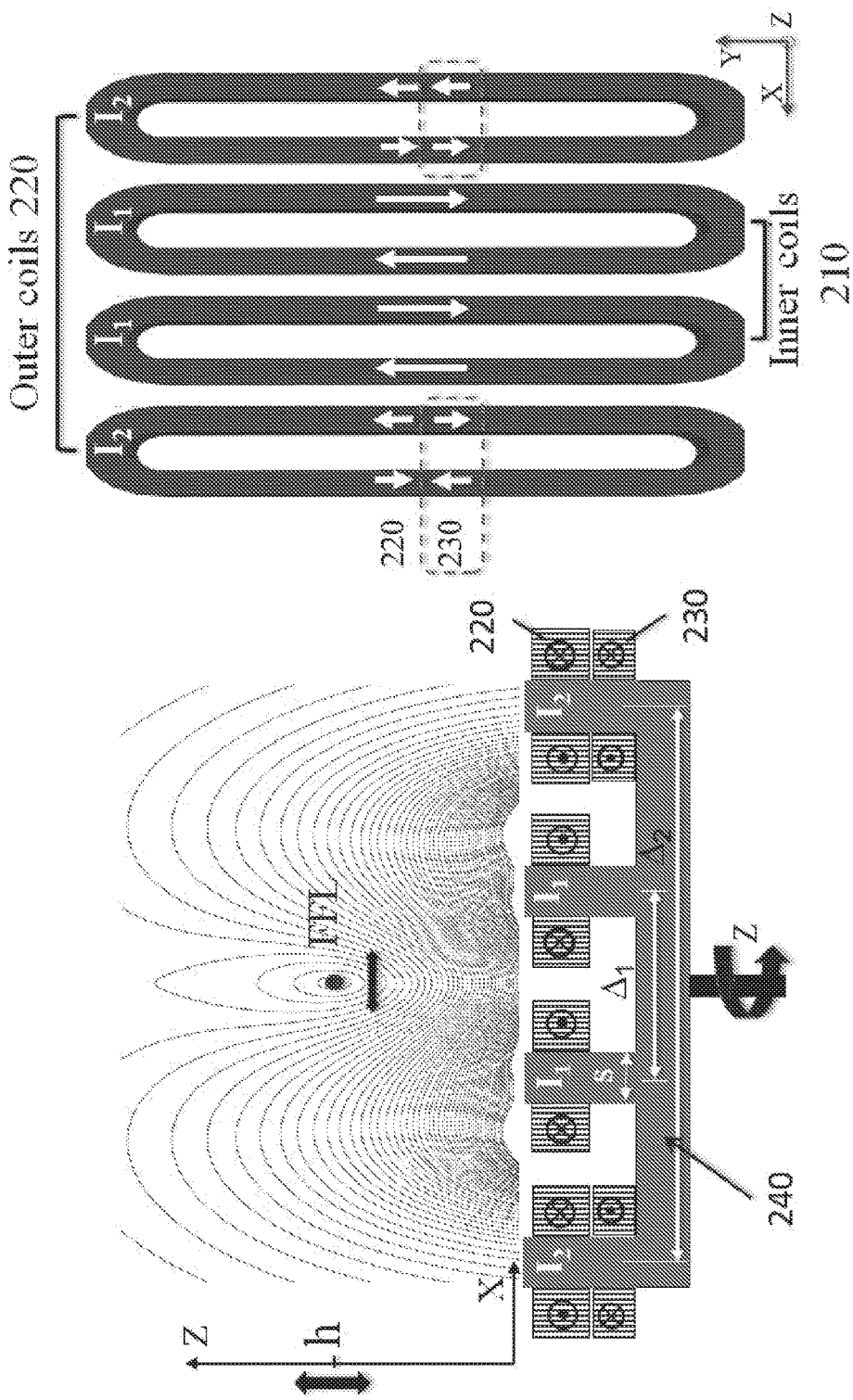
FIG. 2A is a cross-sectional view an arrangement of electromagnetic coils in an exemplary single-sided FFL MPI scanner.
FIG. 2B is a plan view an arrangement of electromagnetic coils and instantaneous current patterns in an exemplary single-sided FFL MPI scanner.

An arrangement of selection coils for a single-sided 3D FFL MPI scanner is shown in FIG. 2A and FIG. 2B. The selection coils consist of (but are not limited to) four coils that are elongated along the Y-axis, displaced from one another along the X-axis, and that are parallel to each other. Although there are several available current driving schemes the illustrated example is sufficient to create the FFL a few millimeters to centimeters away from the surface of the coils. Furthermore, by switching the relative current between the inner and outer pairs of coils the FFL could be made to travel along the Z-axis, thus encoding the depth inside the subject or object. The in-plane (X-Y) encoding is done through projection image reconstruction by mechanical rotation of the device around the Z-axis using rotating fixture 240 upon which the electromagnetic coils are mounted. Rotation of the device occurs about the Z-axis at an axis centered between the coils in both the X-axis and Y-axis. FIG. 2B illustrates implementation of the selection coils design for a single-sided scanner. The example in FIGS. 2A and 2B shows four element selection coils with a certain current pattern as follows: the two inner coils 210 have equal currents L with opposite directions: the clockwise and counterclockwise (as seen by the subject or object) and the outer two coils 220 have equal currents $I_2$ but both are in a counterclockwise direction. Such a current pattern produces an FFL at a certain distance from the coil surface. The current amplitude $I_1$ defines the strength of the field gradient and the difference between the amplitudes $I_1$ and $I_2$ controls the depth of FFL (along Z-axis). The image encoding trajectories could be produced in a similar fashion as in a symmetric FFL device as described with reference to FIGS. 1A-1D above. The same selection outer coils could be used as the drive coils by modulating the current with a 20-100 kHz drive current. The receive coils (not shown) could be positioned on the surface of the device. A larger number of the electromagnetic coils could be utilized to produce higher depth FFL without compromising gradient strength to enclose a larger FOV. In addition, the inner coils 210 could be implemented with ferromagnetic cores to boost the gradient strength per unit current or replaced or supplemented with a pair of permanent magnets.

In the electromagnet arrangement for the single-sided 3D FFL MPI scanner illustrated in FIGS. 2A and 2B, four of the coil elements, two inner coil elements 210 and two outer coil elements 220 are arranged parallel to one another in a common plane displaced from one another about the X-axis and having elongated shape such that the length of the coils in the Y-axis is substantially greater than the width of the coils in the X-axis. The axes of each of coils 210, 220 are parallel to the Z-axis. An additional set of coils 230 may be provided disposed directly below and coaxial with the outer coils 220, also with axes parallel to the Z-axis, although in some embodiments, the coils 230 may be displaced in the X-axis relative to outer coils 220. As illustrated in FIG. 2B, the current in coils 230 has out-of-phase pattern while the current in outer coils 220 has in-phase pattern. The current in coils 230 may oscillate to displace the FFL back and forth along the X-axis.

The coils of the electromagnets are formed of a low resistivity material, for example, copper and in some embodiments may be formed of superconducting materials. In one example, the coils of the electromagnets comprise copper tape having a width of about 6 mm and a height of about 13 mm. In other examples, the coils of the electromagnets comprise Litz wires that may include multiple filaments with various cross-sections. The electromagnets may include from about 20 to about a few hundred windings of conductive material and may have an impedance of less than about 100 mΩ, for example, between about 10 mΩ and about 100 mΩ and an inductance of about 10 µH to about 100 µH. In examples utilizing superconducting coils for the electromagnets, the electrical resistance of the coils would be zero. The electromagnets may, in use, be driven with currents between about 100 A and about 1,000 A or more. The electromagnets may include active cooling systems, for example, coolant lines passing through the coils or built into the coils themselves to circulate a coolant, for example, water, oil, or another coolant through the coils during operation. In some examples, the electromagnets are coreless, or include cores free of magnetic material. In some examples each of coils 210, 220, and 230 are identical in structure and dimensions. In other examples, coils 210 are identical in structure and dimensions to one another, coils 220 are identical in structure and dimensions to one another, and coils 230 are identical in structure and dimensions to one another, but at least one of coils 210, 220, and 230 differ in structure and/or dimensions from at least one other of coils 210, 220, and 230.

In accordance with one or more embodiments, of a single-sided 3D FFL MPI scanner the selection coils consist of four straight parallel coils. The generation of FFL works as following: two inner coil elements 210 with equal DC current with amplitudes $I_1$ create a field gradient at certain height from the surface, while two outer coils 220 with current amplitudes $I_2$ create oscillating bias field that moves the height of FFL. Thus, by switching the relative current between the inner 210 and outer 220 pairs of coils the FFL could oscillate along the Z-axis encoding the depth inside the subject or object while the gradient strength could be kept relatively constant by dynamically adjusting the amplitude of $I_1$. The base height (depth) of FFL is defined by the width of each coil element and the gap between the coils. The in-plane (X-Y) encoding is done through projection imaging by mechanical rotation of the device around the z-axis (up to 180°). The two inner coils 210 could also be replaced with permanent magnets with alternating poles or wound around ferromagnetic cores or use superconducting coils thus reducing the power consumption of such a device.

More outer coil elements 220, 230 could be utilized for additional fine control of homogeneity (shimming) of the field.

To evaluate the magnetic field generated by the single sided elongated electromagnets mathematical simulations were carried out using Wolfram Mathematica® software with Radia package (ESRF, France). The package allows calculation of the magnetic field B of electromagnetic coils by utilizing boundary Integral Methods.

A. Static FFL Generator

First we consider a static FFL generator including two (inner) electromagnetic coils as illustrated in FIGS. 2A and 2B, but omitting coils 230. For practical considerations we modeled two identical electromagnetic coils using the properties of the actual materials of a straight magnetic guiding structure with the following dimensions: l=200 mm (straight length), w=24 mm (width) and aspect ratio of 8:33:1. Here, each coil consists of N=25 windings of conducting tape (6.33×0.3 mm$^2$) with the core width s and coil separation of $\Delta_1$=4 s.

Figure 2C:
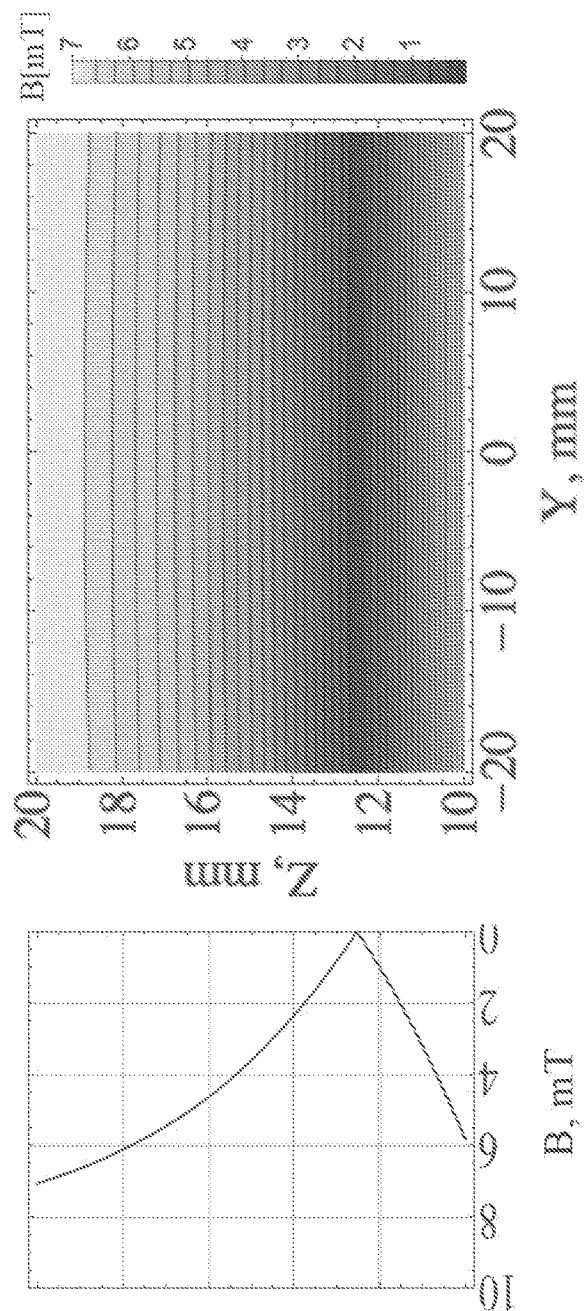
FIG. 2C illustrates results of a simulation of magnetic field quality in the Y-Z plane of an exemplary single-sided FFL MPI scanner design.

FIG. 2C shows simulations of the magnetic field B pattern produced by two inner coils structure. The simulations were done for s=9 mm and a DC current of $I_1$=100 A that generates FFL at h=12:5 mm with a field gradient of $G_z$=2 T/m. The practical region of operation is limited by L≈4 cm along FFL (Y-axis) without sacrificing resolution as defined by the finite curvature of magnetic field lines. The curvature of FFL depends on the aspect ratio of the coils as is discussed below.

B. FFL Generator for Multidimensional MPI

A design of an MPI device that is capable of multidimensional image encoding was also simulated. The model consists of the same pair of inner coils 210 as illustrated in FIG. 2A and a pair of two identical outer electromagnetic coils 220 as also illustrated in FIG. 2A. For simplicity, we consider static field simulations with instantaneous current patterns of $I_2$. Since the magnetic field B and gradient strength are decreasing with coil separation the simulated outer coils were positioned with the smallest practical separation between each other. For this simulation a $\Delta_2$=10 s was used.

Figure 2D:
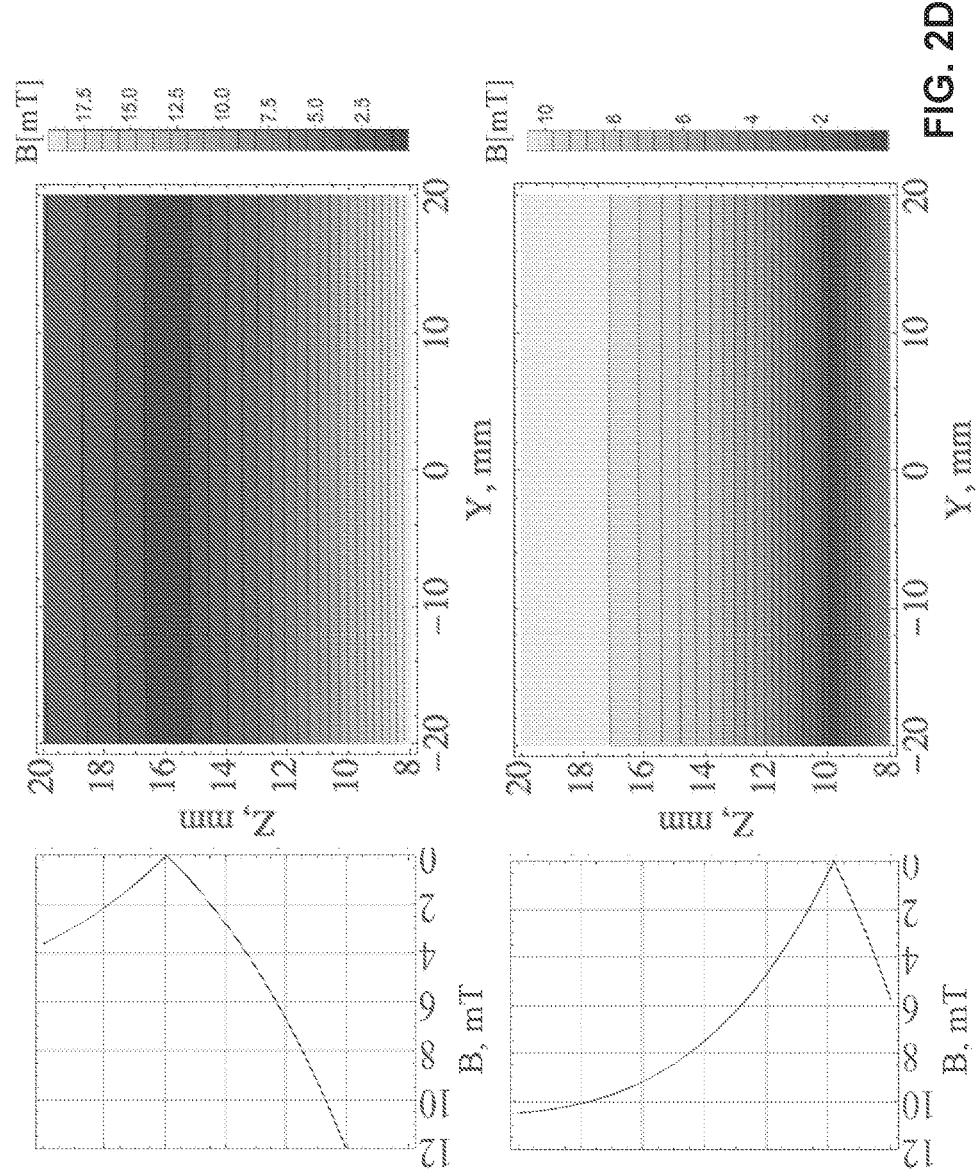
FIG. 2D illustrates results of a simulation of magnetic field strength in the Y-Z plane of an exemplary single-sided FFL MPI scanner design during FFL encoding along the Z-axis.

FIG. 2D shows simulations of the magnetic field pattern for two pairs of electromagnetic coils with the outer ones driven in-phase (the current pattern shown in FIG. 2B for coils 230). In the simulations the current in the inner coils was fixed at $I_1$=100 A and $I_2$ in the outer coils was varied. The upper charts in FIG. 2D show the field patterns for $I_2$=$I_1$=100 A (α=1, positive cycle phase) with the FFL height at 16 mm above the surface and gradient $G_z$=1:25 T/m, and the lower charts in FIG. 2D show the field patterns for $I_2$=−$I_1$=−100 A (α=−1, negative cycle phase) with FFL height at 10 mm above the surface and gradient $G_z$=2.6 T/m respectively. The depth FOV spans Δh=6 mm for α=±1. Due to intrinsic inhomogeneity of the field in the asymmetric topology the gradient values vary with the height that affects the resolution of MPI, therefore current adjustments are necessary. As in the design with fixed geometry, the FFL height only depends on the ratio of the current, however the field gradient depends on the current. One way to correct the gradient to the first order is by dynamically adjusting $I_1$. This algorithm can be implemented by a linear modulation of the current $I_1$ as follows:

$$I_1(t)=16I_0(2-3t/T) \text{ for positive } I_2 \text{ cycles; and}$$

$$I_1(t)=5I_0(5-4t/T) \text{ for negative } I_2 \text{ cycles}$$

where T=1/f and $I_0$=5 A. So for n=1 and positive cycle phase: $I_2$=$I_1$=160 A at h=16 mm and negative cycle: $I_2$=−$I_1$=−75 A at h=10 mm the gradient $G_z$=2 T/m is the same at the boundaries of the FOV.

Similarly we can obtain a larger depth encoding for different current amplitude ratios n. For example, when n=2 at the positive cycle h=20 mm and h=8 mm at the negative cycle phase, so Δh=12 mm, if n=3 then Δh=17 mm, and so on.

Figure 2E:
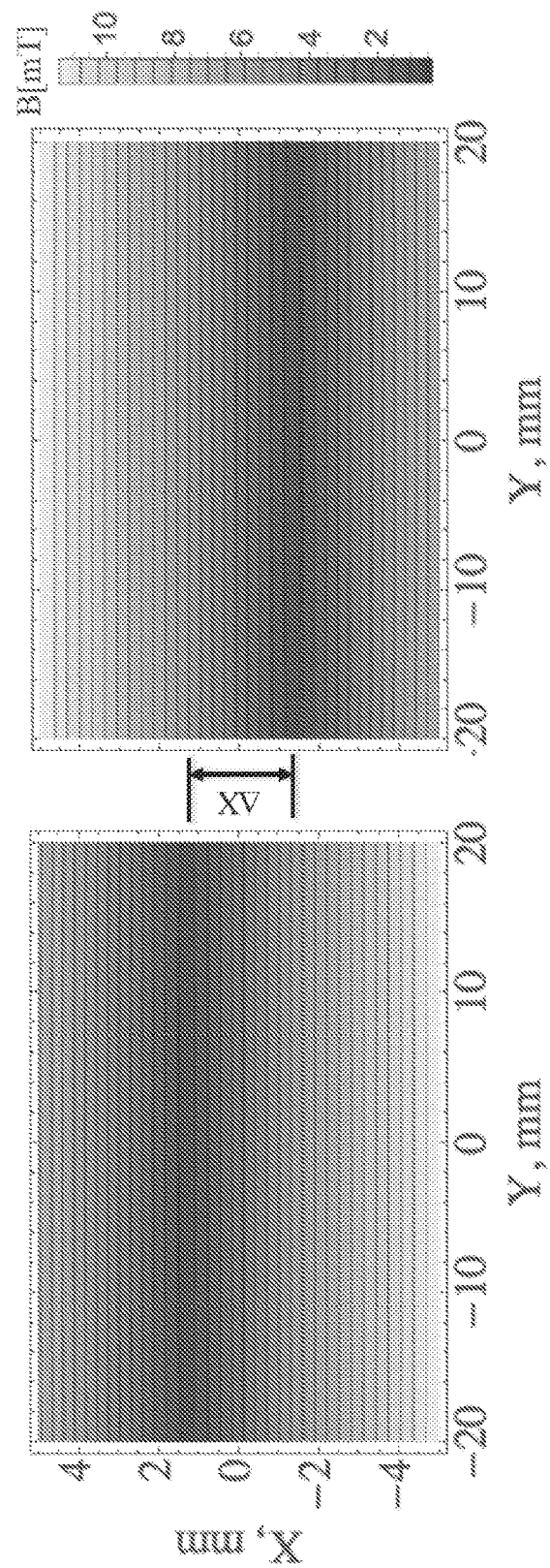
FIG. 2E illustrates results of a simulation of magnetic field strength in the X-Y plane of an exemplary single-sided FFL MPI scanner design during FFL encoding along the X-axis.

The operation of the outer drive coils for in-plane position encoding was simulated. To simulate this regime $I_2$ between the outer coils was changed to be out of phase (the current pattern shown for coils 230 in FIG. 2B), while keeping all the other parameters the same as above. FIG. 2E shows simulation examples of the respective magnetic field pattern. In the simulations the current in the inner coils was set at $I_1$=100 A and $I_2$=±50 A in the outer coils. This simulation demonstrates that the outer drive coils with AC current $I_2$ in combination with the rotation around the Z-axis can encode 2D FOV of 2.5×2.5 mm$^2$, while keeping the field gradient $G_z$ constant. Higher current amplitudes and advanced algorithms could be implemented to provide a sufficiently larger in-plane FOV.

Figure 2F:
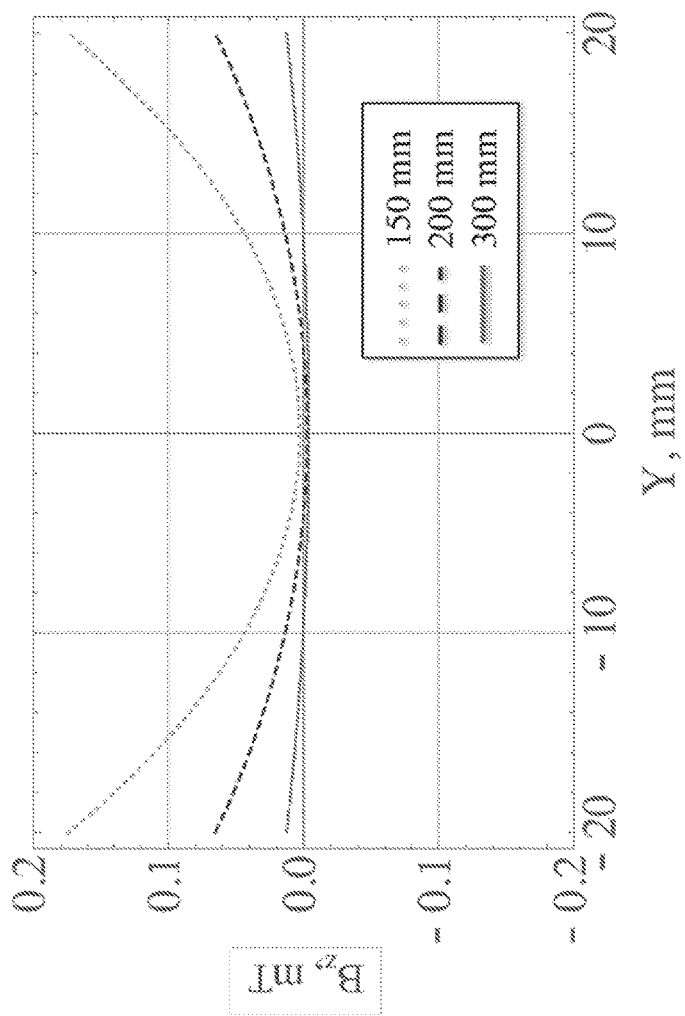
FIG. 2F illustrates results of a simulation of FFL quality of different exemplary single-sided FFL MPI scanner designs.

One of the features of the disclosed design is relatively low longitudinal curvature of the field. The curved magnetic field lines arise due to the finite size of each coil. FIG. 2F shows the simulation study of the FFL curvature versus inner electromagnetic coil (straight part) length. As seen from the simulations, for the coils with lengths l≥200 mm, the divergence of the equipotential lines is less than 100 μT (at $I_1$=100 A) per 2 cm length of FFL, which is tolerable for a practical MPI device.

3. Compact Single-Sided FFL MPI Scanner Based on Permanent Magnets

Figure 3A:
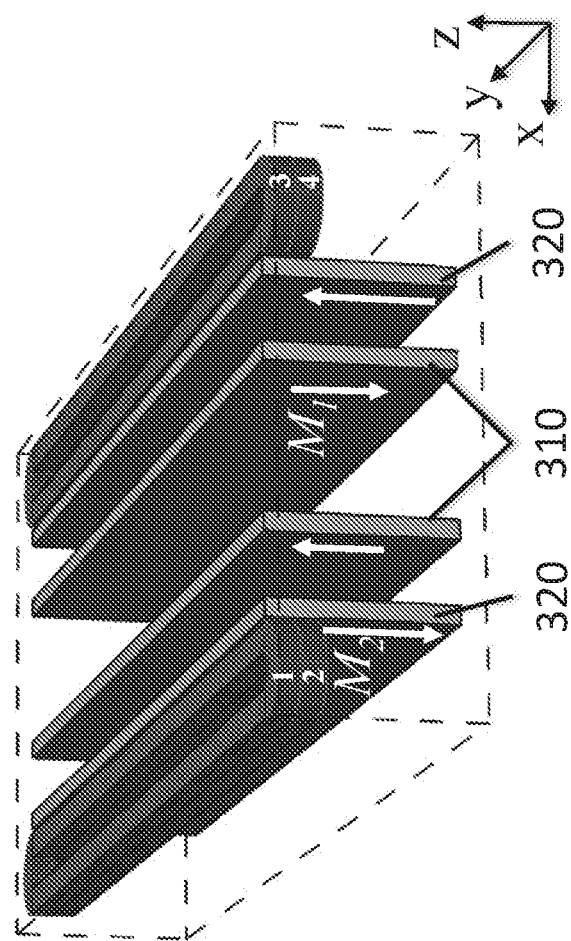
FIG. 3A is an isometric view an arrangement of electromagnetic coils and permanent magnets in an exemplary single-sided FFL MPI scanner.

In accordance with one or more embodiments, a spatial in-plane encoding single-sided device can be also made with a set of elongated (rare earth, e.g., NdFeB or SmCo) permanent magnets. See FIG. 3A illustrating a compact single-sided scanner based on permanent magnets. Four magnets as shown in the figure may produce FFL a few millimeters away from the surface depending on the size and grade of the magnets. The permanent magnets are arranged as follows: two inner magnets 310 have equal strength $M_1$ (magnetization) and two outer magnets 320 have equal strength magnetization $M_2$ so that $M_2 > M_1$. The permanent magnets 310, 320 are vertically poled along the Z-axis. The permanent magnets 310, 320 are rectangular prisms having lengths along the Y-axis as illustrated in FIG. 3A that are significantly greater, for example, about five times greater, about 10 times greater, or about 15 times or more greater than their heights along the Z-axis and significantly greater, for example, about 10 times greater, about 15 times greater, or about 25 times or more greater than their widths along the X-axis. The permanent magnets 310, 320 are arranged parallel to one another and may be substantially or fully equally dimensioned. The permanent magnets 310, 320 are arranged side-by-side along the X-axis. To fulfill the zero field condition the magnetization vector of each adjacent magnet is antiparallel to each other. Such configuration of the magnetizations creates two competing magnetic fields $H_1$ and $H_2$, which are oriented along the X-axis and opposite to each other at the isoplane (YZ, X=0). The FFL is generated along the Y-axis above the surface at z=h for $H_1$(h)=−$H_2$(h).

The gap between the magnets, strengths and the strength difference define the magnetic gradient and height of FFL above the surface. In some examples, a magnetic field with a strong gradient is created by closely positioned two inner magnets 310 that generate rapid field decay along the Z-axis and widely separated strong outer magnets 320 that generate a quasi-uniform field. In practice, the geometry is constrained by the dimensions of the blocks and coils, although the mechanical adjustment of the gaps can be incorporated into the actual device. At the fixed geometry the permanent field tuning is done by the choice of the surface magnetizations. The base height of the FFL is reciprocal to the ratio of magnetizations $m=M_2/M_1$ so for m=1, h→∞, form>>1, h→0. The gradient strength is proportional to the magnitude of the magnetizations, so for fixed m the gradient doubles if both magnetizations double, while the height stays constant. For example, if the gaps between the inner and outer magnets are 14.5 mm and 87 mm respectively, $M_1=0.6/4\pi T\mu_0^{-1}$, $M_2=2/4\pi T\mu_0^{-1}$ then the gradient G=7 T/m at the height h=10 mm.

To offset the magnetic field from the permanent magnets two sets of elongated electromagnetic coils, which may be similar in materials and construction as electromagnetic coils 220 and 230 of FIG. 2A, outside of the outer pair of the permanent magnets 310, 320 as shown in FIG. 3A. The two sets of elongated electromagnetic coils are parallel to the outer permanent magnets and to the inner permanent magnets and have conductors wound about axes that are parallel to the height direction (Z-axis) of the permanent magnets.

The bias magnetic field from the outer electromagnet coils (2, 4) with out-of-phase current pattern shifts the FFL in YZ-plane. These coils can be used as Z-drive coils with AC current:

$$I_z(t)=I_0^z \sin(2\pi f_z t),$$

where $I_0^z$ is the current amplitude that defines the depth encoding, and $f_z$=10–25 kHz is the drive frequency.

For 3-D image encoding a second pair of coils are provided to oscillate the FFL in the YZ-plane. In the disclosed design this X-drive pair of coils (1, 3) is positioned on top of Z-drive coils as shown FIG. 3A. The two X-coils are driven with in-phase AC current according to:

$$I_x(t)=I_0^x \sin(2\pi f_x t)$$

where $I_0^x$ is the current amplitude that defines Δx encoding, and $f_x$=10–25 kHz is the drive frequency. With the appropriately chosen parameters and dimensions of the coils the FFL can be smoothly oscillated along the X-axis. Therefore, by independently driving X- and Z-coils with AC current so that $f_x/f_z=p/k$ for integers p,k, and simultaneous rotation of the device around the Z-axis for projection reconstruction it is possible to encode a 3-D image. Rotation of the device may be achieved by mounting the device on a rotating fixture such as rotating fixture 240 illustrated in FIG. 2A and rotating the rotating fixture such that the magnets and electromagnetic coils are rotated about an axis parallel to the Z-axis and centered in the X-axis and Y-axis between the magnets and electromagnetic coils.

To encode the in-plane image the device may be mechanically rotated around the Z-axis for projection imaging. Additional drive and receive coils could be placed on the surface of the device. Such a device provides fixed height FFL and could be used for specific organ imaging and could be combined with mechanical motion along the Z-axis. This could offer an inexpensive, low power (battery operated), and compact MPI probe available for clinical practice and material survey.

To evaluate the magnetic field generated by the permanent magnets and electromagnetic coils quasistatic simulations were carried out using Wolfram Mathematica® software with Radia package (ESRF France).

A simulation was performed for a static FFL generator that includes four permanent magnets and no electromagnets. For simplicity, in the simulation model all four magnets were modeled as having equal dimensions: length l=300 mm, width w=50 mm, and thickness t=5 mm. The inner and outer magnets' separations were modeled as $\Delta_1$=34.5 mm and $\Delta_2$=69 mm, respectively, and the magnetizations: $M_1=0.5/4\pi T\mu_0^{-1}$, $M_2=\frac{1}{4}\pi T\mu_0^{-1}$ so that m=2. FIGS. 3B and 3C show simulations of the magnetic field B from the complete set of permanent magnets described above. The contour plots of FIG. 3B show the quality of the generated magnetic field and FFL at the height of h=10 mm above the surface of the magnets. The magnetic field magnitude plots along Z-axis and X-axis, illustrated in FIG. 3C, show the respective gradients of the field with the maximum strength G=1.2 T/m. The specified geometry provides a flat FFL over the (−50<y<50) mm region that depends on the aspect ratio of the magnets.

The image encoding examples of the coils assembly design is done with symmetrically located elongated electromagnet coils as shown in FIG. 3A. The top set of the coils denoted as (1, 3) are used as X-drive coils and the bottom pair (2, 4) are used as Z-drive coils. In the quasi-static simulations an electromagnet design was modeled that utilizes a plane conductor. Each simulated electromagnet has the following dimensions: straight length l=300 mm, width w=24 mm, height h=6.4 mm, and core width s=9 mm. The model conductor is made of N=25 windings of conducting tape (6.33×0.3 $mm^2$).

Figure 3D:
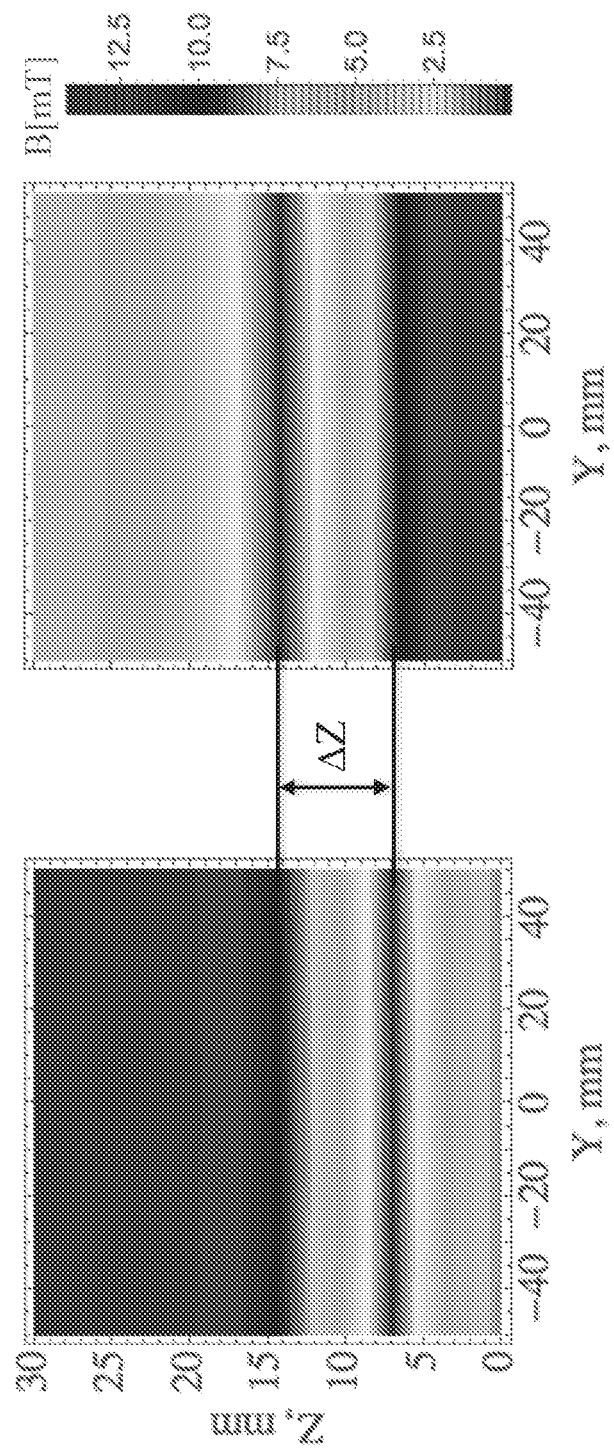
FIG. 3D illustrates results of a simulation of FFL oscillation along the Z-axis in the Y-Z plane of an exemplary single-sided FFL MPI scanner.

The simulations results for the magnetic field of the selection coils operated in combination with Z-drive (2, 4) coils are shown in FIG. 3D. The instantaneous currents $I_z(t)$=−100 A and $I_z(t)$=100 A shift the FFL to z=7 mm and z=14 mm above the surface, respectively. Thus, the peak current of 100 A allows encoding ΔZ=7 mm. The gradient strength, however, does not stay constant over the depth span, which is inherent drawback of single-sided device. So for the low trajectory point G=1.5 T/m and for the upper point G=0.9 T/m. This difference of gradient strength should be taken into the account and corrected at the image reconstruction stage.

Figure 3E:
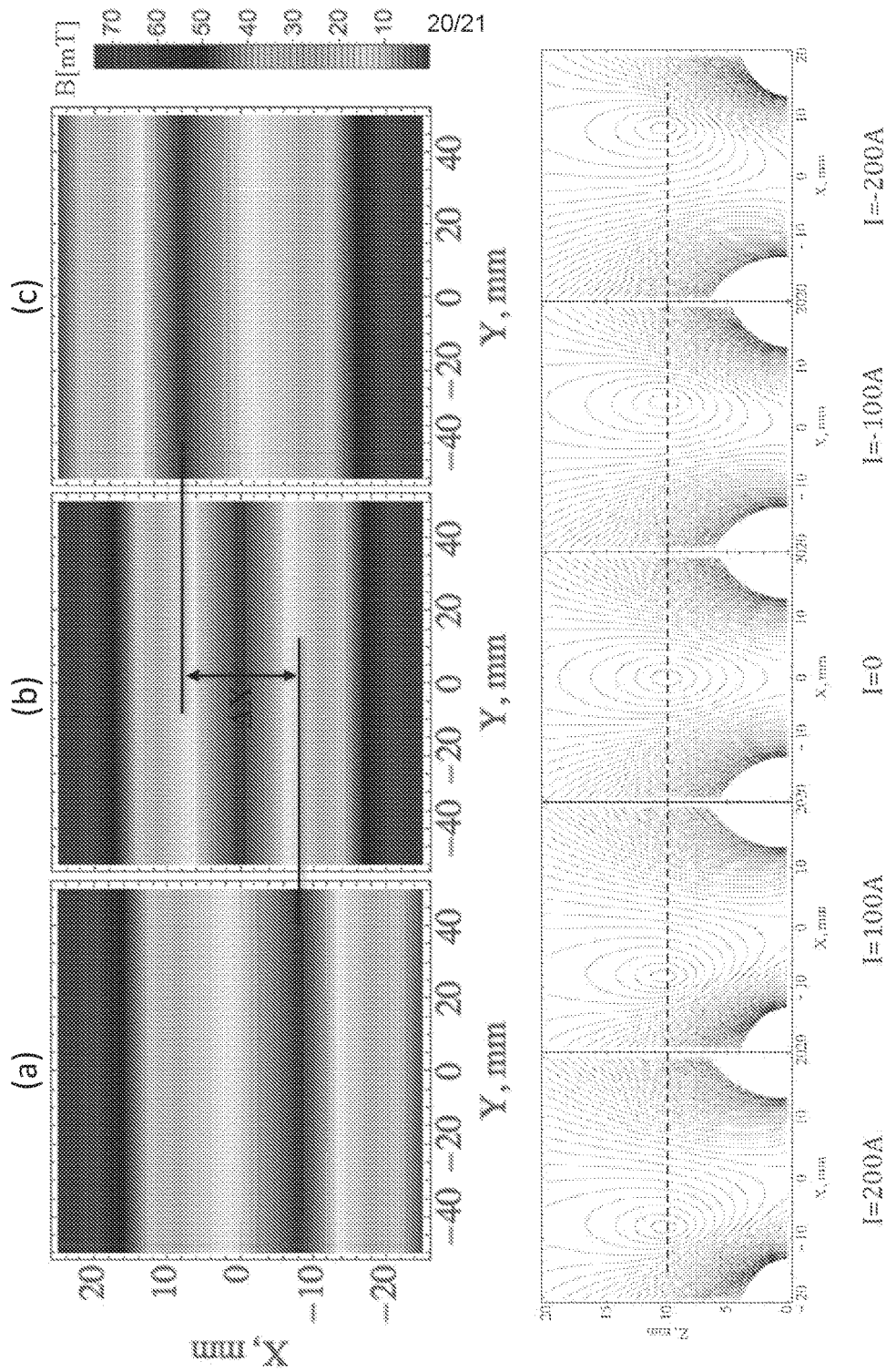
FIG. 3E illustrates results of a simulation of FFL oscillation along the X-axis in the X-Y plane of an exemplary single-sided FFL MPI scanner.

FIG. 3E shows the simulations results from the operation of the selection coils in combination with the X-drive (1, 3) electromagnet coils. The FFL shifts in XY-plane are shown in the top row of FIG. 3E where FFL oscillates from (a) x=−8 mm for $I_x(t)$=200 A to (b) x=0 mm for $I_x(t)$=0 A, and (c) x=8 mm for $I_x(t)$=−200 A, respectively, showing overall image encoding along X-axis over ΔX=16 mm. The bottom row of FIG. 3E shows the FFL trajectory $x(I_x(t))$, while the height above the surface stays constant at z=10 mm for $I_z$=0. The Z-drive coils can be operated at the same time allowing XY-plane encoding.

The above simulations show an example of XY-plane FOV encoding of 16×7 $mm^2$ that for the given system can be linearly scaled with various peak currents. An actual MPI device would benefit from the higher gradient strength that can be obtained for permanent magnets with larger magnetizations, however, to encode the same FOV it would also utilize higher peak currents in both sets of drive coils.

Figure 4:
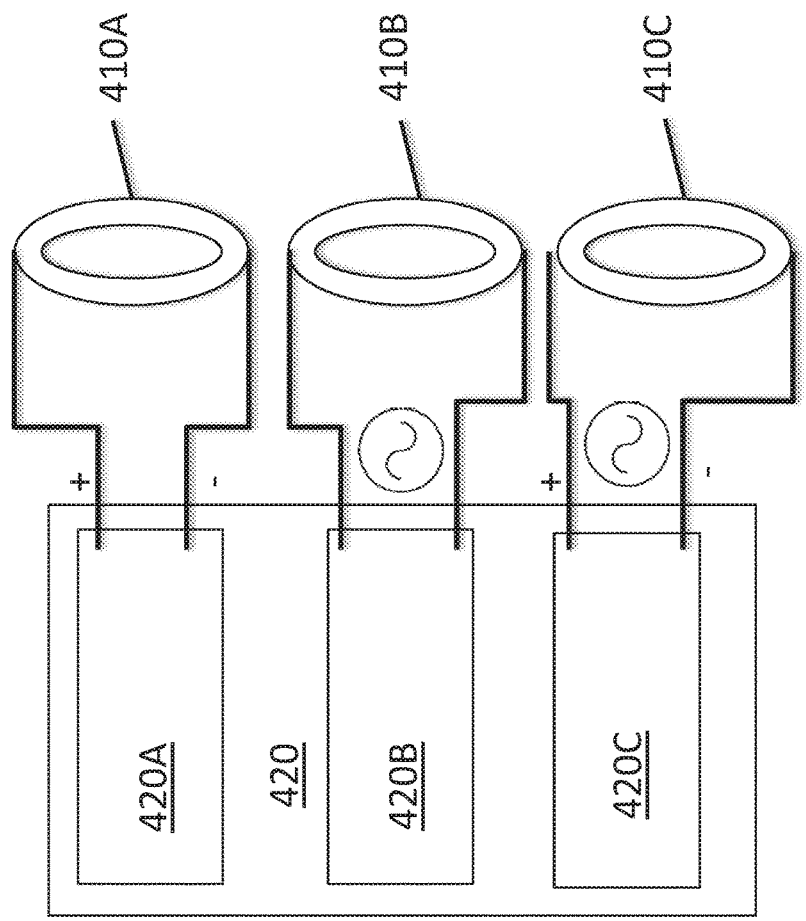
FIG. 4 is a simplified illustration of a current generator for electromagnetic coils of exemplary FFL MPI scanner designs.

Any of the electromagnetic coils, for example, selection coils, focus coils, selection-focus coils, or drive coils utilized in any of the devices disclosed herein, represented as coils 410A, 410B, and 410C in FIG. 4 may be driven or have current provided by a current source with current amplifier or current generator 420 that may also include (low pass or notch) filters and impedance matching circuits. In some examples, different coils may be driven by different sub-circuits 420A, 420B, 420C of the current generator 420 or by different current generators. The current generator 420 may drive the different coils 410A, 410B, and 410C with any of DC current, AC current, or AC current superimposed on DC current depending upon the purpose of the different coils. The current generator 420 may drive the different coils 410A, 410B, and 410C with different current magnitudes, for example, currents up to multiple thousands of Amperes depending upon the purpose of the different coils.

Aspects and embodiments disclosed herein are not limited in application to the details of construction and the arrangement of components set forth in the following description or illustrated in the drawings. Aspects and embodiments disclosed herein are capable of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

The function and advantages of these and other embodiments will be more fully understood from the following non-limiting examples. The examples are intended to be illustrative in nature and are not to be considered as limiting the scope of the embodiments discussed herein.

What is claimed is:

1. A field free line (FFL)-based magnetic particle imaging (MPI) device comprising:
a first set of elongated electromagnets having lengths greater than widths and disposed along a common first axis;
a second set of elongated electromagnets having lengths greater than widths and disposed along a common second axis, the common first axis being parallel to the common second axis and displaced from the common second axis in a direction normal to the common first axis, the second set of elongated electromagnets disposed directly over and overlapping the first set of elongated electromagnets in the direction normal to the common first axis; and
a current generator configured to:
drive a first selection current in a first direction about the common first axis through an elongated electromagnet in the first set of elongated electromagnets; and
drive a second selection current in a second direction about the common second axis through an elongated electromagnet in the second set of elongated electromagnets, the second direction being opposite to the first direction, the elongated electromagnet in the second set of elongated electromagnets being disposed directly over the elongated electromagnet in the first set of elongated electromagnets in the direction normal to the common first axis, the first selection current and the second selection current creating a selection magnetic field defining a field free line between the first set of elongated electromagnets and the second set of elongated electromagnets and parallel to a direction defined by the lengths of the elongated electromagnets.

2. The device of claim 1, wherein the current generator is further configured to:
drive a first focus current superimposed on the first selection current in an elongated electromagnet in the first set of elongated electromagnets; and
drive a second focus current superimposed on the second selection current in an elongated electromagnet in the second set of elongated electromagnets disposed directly over the elongated electromagnet in the first set of elongated electromagnets in the direction normal to the common first axis, the first focus current and second focus current creating a focus magnetic field displacing the field free line from a position centrally located between the first set of elongated electromagnets and second set of elongated electromagnets in a direction defined by widths of the elongated electromagnets.

3. The device of claim 1, wherein the current generator is further configured to drive an excitation field having a frequency of between about 20 kHz and about 100 kHz in at least one of the elongated electromagnets.

4. The device of claim 1, further comprising a drive coil configured to generate an excitation field having a frequency of between about 20 kHz and about 100 kHz in a region defined between the first set of elongated electromagnets and the second set of elongated electromagnets.

5. The device of claim 1, wherein the first set of elongated electromagnets and the second set of elongated electromagnets are mounted on a rotating fixture configured to rotate the first set of elongated electromagnets and the second set of elongated electromagnets about an axis parallel to the common first axis and centrally located between the first set of elongated electromagnets and the second set of elongated electromagnets.

6. The device of claim 5, configured to provide three dimensional imaging of an object disposed between the first set of elongated electromagnets and the second set of elongated electromagnets.

7. The device of claim 1, wherein each of the elongated electromagnets has a length:width ratio of at least 5:1.

8. The device of claim 1, further comprising permanent magnets having magnetic fields that contribute to the selection field.

9. A method of performing field free line (FFL)-based magnetic particle imaging (MPI) of an object, the method comprising:
positioning the object between a first set of elongated electromagnets having lengths greater than widths and disposed along a common first axis and a second set of elongated electromagnets having lengths greater than widths and disposed along a common second axis, the common first axis being parallel to the common second axis and displaced from the common second axis in a direction normal to the common first axis, the second set of elongated electromagnets disposed directly over and overlapping the first set of elongated electromagnets in the direction normal to the common first axis;
driving a first selection current in a first direction about the common first axis through an elongated electromagnet in the first set of elongated electromagnets; and
driving a second selection current in a second direction about the common second axis through an elongated electromagnet in the second set of elongated electromagnets, the second direction being opposite to the first direction, the elongated electromagnet in the second set of elongated electromagnets being disposed directly over the elongated electromagnet in the first set of elongated electromagnets in the direction normal to the common first axis, the first selection current and the second selection current creating a selection magnetic field defining a field free line between the first set of elongated electromagnets and the second set of elongated electromagnets and parallel to a direction defined by the lengths of the elongated electromagnets.

10. The method of claim 9, further comprising:
driving a first focus current superimposed on the first selection current in an elongated electromagnet in the first set of elongated electromagnets; and
driving a second focus current superimposed on the second selection current in an elongated electromagnet in the second set of elongated electromagnets disposed directly over the elongated electromagnet in the first set of elongated electromagnets in the direction normal to the common first axis, the first focus current and second focus current creating a focus magnetic field displacing the field free line from a position centrally located between the first set of elongated electromagnets and second set of elongated electromagnets in a direction defined by widths of the elongated electromagnets.

11. The method of claim 9, further comprising driving an excitation field having a frequency of between about 20 kHz and about 100 kHz in at least one of the elongated electromagnets.

12. The method of claim 11, further comprising exciting magnetic nanoparticles within the object with the excitation field.

13. The method of claim 9, further comprising generating an excitation field having a frequency of between about 20 kHz and about 100 kHz in a region defined between the first set of elongated electromagnets and the second set of elongated electromagnets with a drive coil distinct from the first set of elongated electromagnets and distinct from the second set of elongated electromagnets.

14. The method of claim 9, further comprising rotating the first set of elongated electromagnets and the second set of elongated electromagnets about an axis parallel to the common first axis and centrally located between the first set of elongated electromagnets and the second set of elongated electromagnets.

15. The method of claim 14, further comprising generating a three dimensional image of the object utilizing a magnetic field generated by the first set of elongated electromagnets and the second set of elongated electromagnets.

16. A single-sided field free line (FFL)-based magnetic particle imaging (MPI) device comprising:
two inner elongated electromagnets having lengths greater than widths and displaced from one another in a direction defined by the widths of the two inner elongated electromagnets;
two outer elongated electromagnets disposed on opposite sides of the two inner elongated electromagnets and displaced from the two inner elongated electromagnets in the direction defined by the widths of the two inner elongated electromagnets, each of the two inner elongated electromagnets and the two outer elongated electromagnets being parallel to one another; and
a current source configured to:
generate a first selection current in a first of the two inner elongated electromagnets, the first selection current travelling in a first direction about an axis of the first of the two inner elongated electromagnets;
generate a second selection current in a second of the two inner elongated electromagnets, the second selection current travelling in a second direction about an axis of the a second of the two inner elongated electromagnets, the second direction being opposite the first direction;
generate a third selection current in a first of the two outer elongated electromagnets, the third selection current travelling in a third direction about an axis of the first of the two outer elongated electromagnets; and
generate a fourth selection current in a second of the two outer elongated electromagnets, the fourth selection current travelling in the third direction about an axis of the second of the two outer elongated electromagnets, the first selection current, second selection current, third selection current, and fourth selection current generating a magnetic field having a field free line parallel to the lengths of the elongated electromagnets displaced from surfaces of the elongated electromagnets in a direction parallel to the axes of the elongated electromagnets.

17. The device of claim 16, wherein the two inner elongated electromagnets and the two outer elongated electromagnets are disposed in a common plane.

18. The device of claim 16, configured to provide three dimensional imaging of an object disposed on a same side of the device as the field free line.

19. The device of claim 16, further comprising:
a first focus elongated electromagnet disposed adjacent the first of the two outer elongated electromagnets; and
a second focus elongated electromagnet disposed adjacent the second of the two outer elongated electromagnets, the current generator configured to generate focus currents in the first and second focus elongated electromagnets that create a magnetic field causing the field free line to be displaced in a direction defined by the widths of the two inner elongated electromagnets and the two outer elongated electromagnets.

20. The device of claim 16, wherein the two inner elongated electromagnets and two outer elongated electromagnets are disposed on a rotating fixture configured to rotate the two inner elongated electromagnets and two outer elongated electromagnets about an axis parallel to the axes of the two inner elongated electromagnets and two outer elongated electromagnets and centrally located between the two inner elongated electromagnets and two outer elongated electromagnets.

21. The device of claim 16, wherein each of the two inner elongated electromagnets and two outer elongated electromagnets have length:width aspect ratios of at least 5:1.

22. The device of claim 16, further comprising permanent magnets having magnetic fields that contribute to the selection field.

23. A method of performing field free line (FFL)-based magnetic particle imaging (MPI) of an object, the method comprising:
disposing the object on a side of a FFL-based MPI imaging device including:
two inner elongated electromagnets having lengths greater than widths and displaced from one another in a direction defined by the widths of the two inner elongated electromagnets; and
two outer elongated electromagnets disposed on opposite sides of the two inner elongated electromagnets and displaced from the two inner elongated electromagnets in the direction defined by the widths of the two inner elongated electromagnets, each of the two inner elongated electromagnets and the two outer elongated electromagnets being parallel to one another;
generating a first selection current in a first of the two inner elongated electromagnets, the first selection current travelling in a first direction about an axis of the first of the two inner elongated electromagnets;

generating a second selection current in a second of the two inner elongated electromagnets, the second selection current travelling in a second direction about an axis of the a second of the two inner elongated electromagnets, the second direction being opposite the first direction;

generating a third selection current in a first of the two outer elongated electromagnets, the third selection current travelling in a third direction about an axis of the first of the two outer elongated electromagnets; and generating a fourth selection current in a second of the two outer elongated electromagnets, the fourth selection current travelling in the third direction about an axis of the second of the two outer elongated electromagnets, the first selection current, second selection current, third selection current, and fourth selection current generating a magnetic field having a field free line parallel to the lengths of the elongated electromagnets displaced from surfaces of the elongated electromagnets in a direction parallel to the axes of the elongated electromagnets.

24. The method of claim 23, further comprising generating focus currents in first and second focus elongated electromagnets disposed adjacent the first and second outer elongated electromagnets, respectively, that create a magnetic field causing the field free line to be displaced in a direction defined by the widths of the two inner elongated electromagnets and the two outer elongated electromagnets.

25. The method of claim 23, further comprising rotating the two inner elongated electromagnets and two outer elongated electromagnets about an axis parallel to the axes of the two inner elongated electromagnets and two outer elongated electromagnets and centrally located between the two inner elongated electromagnets and two outer elongated electromagnets.

26. The method of claim 25, further comprising generating a three dimensional image of the object.

27. The device of claim 1, wherein the device is configured for use in cancer diagnostics or cancer staging.

28. The method of claim 9, wherein the method is used for cancer diagnostics or cancer staging.

29. The device of claim 16, wherein the device is configured for use in cancer diagnostics or cancer staging.

30. The device of claim 29, wherein the device is configured for use in breast cancer screening and staging.

31. The method of claim 23, wherein the method is used for cancer diagnostics or cancer staging.

* * * * *